US009895174B2

(12) United States Patent
Ozdil et al.

(10) Patent No.: US 9,895,174 B2
(45) Date of Patent: Feb. 20, 2018

(54) ORTHOPEDIC STIFFENING DEVICE

(71) Applicant: Empire Technology Development LLC, Wilmington, DE (US)

(72) Inventors: Deniz Ozdil, Eveleigh (AU); Phillip Marathakis, Eveleigh (AU); Gregory James Roger, Eveleigh (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 15/127,086

(22) PCT Filed: Mar. 18, 2014

(86) PCT No.: PCT/US2014/031037
§ 371 (c)(1),
(2) Date: Sep. 19, 2016

(87) PCT Pub. No.: WO2015/142320
PCT Pub. Date: Sep. 24, 2015

(65) Prior Publication Data
US 2017/0119439 A1 May 4, 2017

(51) Int. Cl.
*A61B 17/70* (2006.01)
(52) U.S. Cl.
CPC ........ *A61B 17/7049* (2013.01); *A61B 17/701* (2013.01); *A61B 17/7032* (2013.01); *A61B 17/7052* (2013.01)
(58) Field of Classification Search
CPC .......................... A61B 17/7049; A61B 17/7059
See application file for complete search history.

(56) References Cited

U.S. PATENT DOCUMENTS

| 5,092,893 | A | * | 3/1992 | Smith | A61B 17/7052 |
| | | | | | 606/290 |
| 5,531,747 | A | * | 7/1996 | Ray | A61B 17/7055 |
| | | | | | 606/278 |

(Continued)

FOREIGN PATENT DOCUMENTS

| CN | 202458646 U | 10/2012 |
| RU | 2372868 C1 | 11/2009 |

(Continued)

OTHER PUBLICATIONS

International Search Report and Witten Opinion for International Application No. PCT/US2014/031037 dated Sep. 2, 2014, pp. 10.

*Primary Examiner* — Ellen C Hammond
*Assistant Examiner* — Stuart S Bray
(74) *Attorney, Agent, or Firm* — The Juhasz Law Firm, P.C.

(57) ABSTRACT

A stiffening device useful for orthopedic stabilization assemblies. The present disclosure provides an apparatus and methods for stiffening the rods and screws typically used for correction of orthopedic defects, such as curvature of the spine. An out-of-plane stiffener is attached to the rods and screws in a plurality of locations, thus reducing the tendency of the rods to move. A stiffener is located in a plane posterior to the rods and screws. The stiffener connects to the rods with adjustable but rigid connections and prevents the rods from bending in the sagittal and coronal planes. This prevents rotation and twisting of the rods and thus the vertebrae into which they are implanted. The stiffeners of the present disclosure may also be attached to pedicle screws only. This helps to correct lordosis and kyphosis bending, as well as scoliosis-type bending. The stiffeners may also be used for cranial and facial applications.

18 Claims, 13 Drawing Sheets

(56) References Cited

U.S. PATENT DOCUMENTS

| | | | | |
|---|---|---|---|---|
| 6,402,751 | B1* | 6/2002 | Hoeck | A61B 17/7049 606/250 |
| 7,294,129 | B2* | 11/2007 | Hawkins | A61B 17/7037 606/86 A |
| 8,177,814 | B2* | 5/2012 | Predick | A61B 17/7044 606/250 |
| 8,758,411 | B1* | 6/2014 | Rayon | A61B 17/7004 606/259 |
| 9,693,808 | B2* | 7/2017 | Fauth | A61B 17/7032 |
| 2006/0089644 | A1* | 4/2006 | Felix | A61B 17/7037 606/250 |
| 2007/0179503 | A1* | 8/2007 | Ferree | A61B 17/70 606/263 |
| 2008/0146111 | A1* | 6/2008 | Pringle | G10K 15/06 445/2 |
| 2008/0243185 | A1* | 10/2008 | Felix | A61B 17/7032 606/246 |
| 2009/0204151 | A1* | 8/2009 | Bracken | A61B 17/7049 606/246 |
| 2009/0326592 | A1* | 12/2009 | Butler | A61B 17/7058 606/286 |
| 2010/0010545 | A1* | 1/2010 | Park | A61B 17/7052 606/278 |
| 2010/0076493 | A1* | 3/2010 | Fauth | A61B 17/1671 606/279 |
| 2012/0029566 | A1* | 2/2012 | Rezach | A61B 17/7038 606/264 |
| 2012/0035659 | A1* | 2/2012 | Barrus | A61B 17/7049 606/251 |
| 2012/0150230 | A1* | 6/2012 | Felix | A61B 17/7049 606/250 |
| 2013/0053888 | A1* | 2/2013 | Torres | A61B 17/7049 606/252 |
| 2013/0296939 | A1* | 11/2013 | Perkins | A61B 17/7068 606/249 |
| 2014/0020333 | A1* | 1/2014 | Knight | A61B 17/0642 53/425 |
| 2014/0046372 | A1* | 2/2014 | Ibrahim | A61B 17/7034 606/250 |
| 2015/0335361 | A1* | 11/2015 | Henderson, Sr. | A61B 17/7059 606/250 |
| 2016/0058476 | A1* | 3/2016 | Sournac | A61B 17/7032 606/267 |
| 2017/0065306 | A1* | 3/2017 | Fauth | A61F 2/4405 |
| 2017/0119439 | A1* | 5/2017 | Ozdil | A61B 17/7049 |
| 2017/0164983 | A1* | 6/2017 | Khajavi | A61B 17/7049 |

FOREIGN PATENT DOCUMENTS

| | | |
|---|---|---|
| RU | 2372869 C1 | 11/2009 |
| RU | 2010142140 A | 4/2012 |
| WO | 2009158622 A1 | 12/2009 |

* cited by examiner

ORTHOPEDIC STIFFENING DEVICE

CROSS-REFERENCE TO RELATED APPLICATION

This application is a U.S. National Stage filing under 35 U.S.C. § 371 of International Application No. PCT/US2014/031037, filed Mar. 18, 2014, which is hereby incorporated by reference in its entirety.

TECHNICAL FIELD

The technical field of the disclosure relates to orthopedic medical and veterinary devices.

BACKGROUND

Spinal fusion surgery is commonly performed to treat degenerative spinal disease. Such procedures have also become necessary among children, the pediatric population, as well as patients who have been injured, the trauma population. In addition, spinal fusion surgery may be indicated for patients with spinal instability and patients with congenital defects. Spinal fusion surgery is commonly performed to treat degenerative disc disease, disc herniation, stenosis, spinal column collapse or instability, spinal trauma or compression fractures, scoliosis and kyphosis and spondylolysis. The incidence of spinal surgery is on the rise in the United States and elsewhere, as indicated by the tremendous increases in the number of procedures for lumbar fusion surgery, among others.

In addition to spinal surgery, other orthopedic procedures have also been on the increase, such as hip and knee procedures. In addition to the increased incidence and prevalence of orthopedic disease in the United States, these maladies have found increases world-wide, as populations live longer and become more demanding of medical treatment. As a result, increased attention has been focused on the effectiveness of these procedures. Improvement is needed both in fusion-type procedures as well as non-fusion type procedures, such as disc replacement.

Unless otherwise indicated herein, the materials described in this section are not prior art to the claims in this application and are not admitted to be prior art by inclusion in this section.

SUMMARY

Technologies are herein described for stiffening devices and stiffening procedures that are useful with orthopedic stabilization devices for curing orthopedic defects or relieving orthopedic trauma in patients. A stiffening device for attachment to an orthopedic fixation device includes a stiffener, also known as a stiffening member, and a plurality of legs. Each leg includes a first portion that is configured to connect to the orthopedic fixation device and a second portion that is configured to connect to the stiffener. The stiffener is configured to provide an out-of-plane area moment of inertia with respect to the orthopedic fixation device, thereby making the stiffener and the orthopedic fixation device more resistant to bending and torsion. Each leg is configured to adjust the out-of-plane area moment of inertia of the stiffener with respect to the orthopedic fixation device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
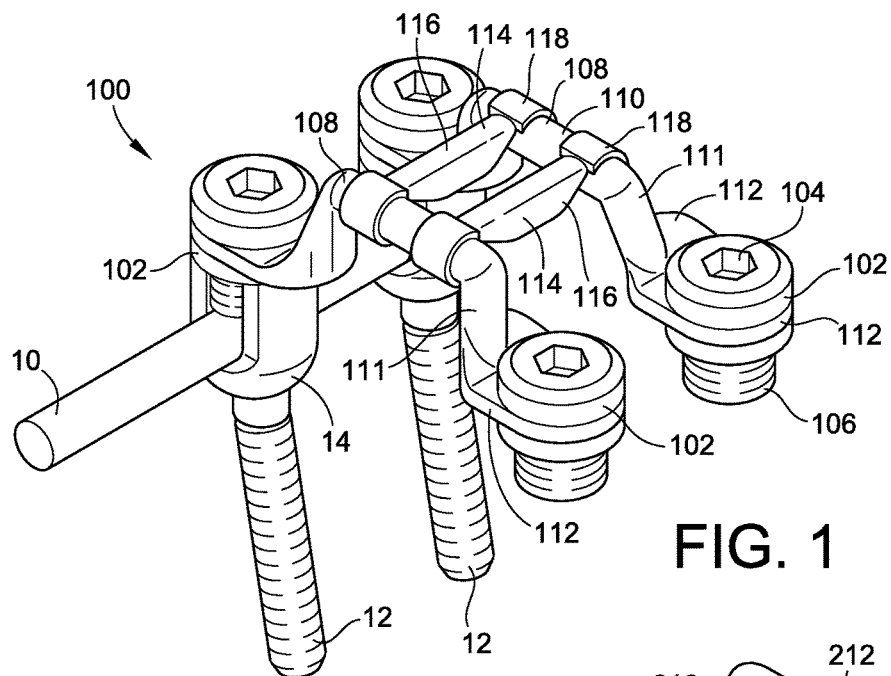
FIG. 1 is a simplified view of an orthopedic stiffening device attached to fusion rods and pedicle screws of an orthopedic fixation device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Technologies are generally described for stiffening members and associated hardware for stiffening an orthopedic fixation device placed into a person to immobilize an area of the body. A stiffening device for attachment to an orthopedic fixation device includes a stiffener and a plurality of legs. Each leg includes a first portion that is configured to connect to the orthopedic fixation device and a second portion that is configured to connect to the stiffener. The stiffener is configured to provide an out-of-plane area moment of inertia with respect to the orthopedic fixation device, thereby making the orthopedic fixation device more resistant to bending and torsion. Each leg is configured to adjust the out-of-plane area moment of inertia of the stiffener with respect to the orthopedic fixation device.

An example of a typical orthopedic fixation device includes a pair of fixation or fusion rods, e.g., for a spinal fusion procedure, such as in the cervical, thoracic or lumbar segment, while other devices such as wires and cables may be used instead or additionally. The rods are typically sized to span two or more vertebrae in order to fix or stabilize the vertebrae to allow fusion of the vertebrae and thus remedy a spinal disorder that prevents the vertebrae from their proper spacing or vertical orientation. In other procedures, the rods are used to stabilize the vertebrae and prevent unwanted movement. The rods are typically secured to the subject's vertebrae by bone fastening devices such as pedicle screws inserted into the pedicles of the vertebrae. In a typical procedure, the rods are joined to both sides of each vertebra spanned by the rods and for which stabilization is desired. The rods may be round in cross section or other shapes, such as square or hexagonal. Connectors to these rods must be matched to their cross sectional shape.

In typical devices in the present state of the art, the rods are placed immediately posterolaterally to the vertebrae and attempts may be made to stiffen them by placing connectors between the rods, perhaps with several connectors spanning the vertebrae segments along the length of the rods. As noted, some devices may span only two vertebrae, in which case there may be only four pedicle screws used, two for each of the vertebrae. Other medically-suitable screws, hooks, tapes, wires and other connection means may also be used for this purpose. In these or in longer orthopedic fixation devices, such as those spanning more than two vertebrae, it may be desired to further stabilize or stiffen the positions of the rods with respect to each other.

Thus, cross connectors may be used to help stiffen the device, e.g., reinforcing bars secured to the fusion rods by grub screws or set screws. If a reinforcing bar is secured to both fusion rods, it is relatively easy to understand that the bar lessens the degrees of freedom of the rods and spine by fixing the distance between the rods and thus prevents the rods from nearing each other or from moving farther apart. This is because the bar has a fixed length that will not change and hence the fused portions of the spine will not move along the fixed length under normal stresses and strains from the user, as the user moves about and bends his or her back while exercising, walking, running, working, and so forth. However, the rods are otherwise allowed to move, and hence the fused portions of the spine are allowed to move with respect to each other.

For example, as one looks behind one's back, a rotational movement is imparted to the vertebrae. When one puts one shoulder higher than another, lateral flexion (abduction) and reduction (adduction) occur in the spine. As one bends, flexes or stretches, the vertebrae, and to a lesser extent the rods, may bend in a lordotic or kyphotic direction, i.e., with the spine curving inwardly or outwardly, while it would be preferable to allow very little such movement. Other undesirable movement may include out-of plane movement of the rods, or relative movement of the rods with respect to each other, such as those imparted by rotational movement of the spine. While no rods are perfectly aligned in a plane, the two rods typically used for fusion procedures may be said to lie roughly in a plane. When the patient moves and exercises, the rods may move out of the approximate plane they occupy. A reinforcing bar, attached to the rods at only one point each, may not be able to add much stiffening in such a situation.

Instead of a reinforcing bar, a reinforcing plate may instead be used, e.g., a stiff plate attached to each rod at two or more points. A plate would add additional stiffness and would prevent any movement in which the rods move independently of each other. However, the rods are still free to move in and out of the plane. In particular, the rods are still subject to disruptive loads, such as by spine rotation and translational loads as the person goes about their daily functions. From the foregoing, it is apparent that conventional orthopedic fixation devices include a set of rods. Any two or more rods of the device lie approximately in, and hence define, a plane. The cross-connectors, reinforcing bars, or other stiffening devices are placed in, or close to, the plane defined by the two or more rods and are connected to the two or more rods. The placement of conventional stiffening devices onto rods generally provides very little force to fix the position of the rods with respect to torsional, twisting, flexing, or other forces that may be imparted to the rods from outside of the plane. Hence, conventional orthopedic stiffening devices provide little resistance to movement of the rods, such as torsion, twisting and flexing of the rods. These forces are important in stabilizing the patient's spine or other body parts in place during the post-operative period.

Having thus introduced the background for an out-of-plane orthopedic stiffening device, we now turn to additional features that are provided by this disclosure.

In describing this disclosure more fully, we make reference to the accompanying drawings, in which illustrative embodiments of the present disclosure are shown. This disclosure may, however, be embodied in a variety of different forms and should not be construed as so limited by the drawings.

FIG. 1 depicts a perspective view of an out-of-plane orthopedic stiffening device 100. The orthopedic stiffening device 100 is intended to stiffen an orthopedic fixation device that includes fusion rods 10 (one per side, only one shown in FIG. 1) and several pedicle screws 12. The fusion rods 10 are secured to pedicle screws 12. Pedicle screws 12 are threaded into pedicles of the vertebrae of a patient, in one embodiment. The pedicle screws 12 include an upper portion 14 or screw head for mounting the fusion rods 10. Other designs of pedicle screw have offset mounts for the attachment to the rod, achieving much the same effect. In the embodiment shown, the pedicle screws are also used to mount the orthopedic stiffening device as well as the orthopedic fixation device, of which they are a part.

Orthopedic stiffening device 100 includes two out-of-plane stiffeners 114, which in this embodiment are two substantially parallel rods or bars. The orthopedic stiffening device also includes U-shaped legs 108 and fasteners 102. The out-of-plane stiffeners 114 are secured to legs 108, which are in turn fastened to the upper portions 14 of the pedicle screws 12. In other embodiments, such as those shown in FIGS. 13-14, the legs connect to the rods through ball-and-socket mechanisms, which may be thought of as a type of snap-fit, or by clamping or collet means, which are less adjustable, but more rigid. Still other connecting and locking mechanisms may be used for these applications. The stiffeners 114 each include a body 116, such as the cross-connecting body depicted, and connector interfaces or ends 118 for connecting to the legs 108. The legs 108 are adjustable as described below. Details on the adjustment of the legs and other details and their interconnection shown in FIG. 1 as well as their operation are explained in greater detail below.

The two out-of-plane stiffeners 114 are effectively stiffeners that lie in a plane that is effectively different from the plane defined by two or more rods. The plane defined by the two or more rods has been previously explained. Hence, the two out-of-plane stiffeners advantageously introduce off-planar forces for use in fixing two or more rods with respect to each other. These off-planar forces are different from and additional to the planar forces that are introduced by conventional stiffeners. More specifically, the out-of-plane stiffeners advantageously introduce an out-of-plane area moment of inertia that resists out-of-plane stress components of force, such as vertical stress components created by the spine and hence stabilizes the spine with respect to the orthopedic fixation device. The one or more out-of-plane stress components of force are useful in keeping the rods from off-planar movements with respect to each other. Such off-planar movements include torsion, twisting and flexing. By reducing such off-planar movements, the disclosed stiffening device of this disclosure increases stabilization of the patient's spine or other body parts in place during the post-operative period.

In use, fusion rods 10 are illustratively intended for placement just posterior to (rearward from) the vertebrae of the patient into whom the device is implanted (not shown). Thus, the rods will be secured in place with mounting screws, such as pedicle screws, as shown in FIG. 1. The rods may also be attached to the pedicle screws through offset attachment means, requiring other iterations of the attachment of the stiffening device (Ref. Medtronic's TSRH 3DX™ system for lumbar spine) Other bone fastening means, such as hooks and wires may also be used. Typically, rods are placed on either side of the spine and are secured with pedicle screws placed into the vertebrae, the rods separated by about 1.5 to 2 cm, although other separation distances may be appropriate. Fasteners attach the legs 108 to the rods so as to hold the rods and the stiffener to each other. The legs 108 are adjusted to adjust the distance between the rods and the out-of-plane stiffeners in a manner described later in this disclosure. The out-of-plane stiffeners illustratively provide an out-of-plane force that is resistive to bending of the spine. Hence, adjustment of the legs increases or decreases the out-of-plane force that is imparted to the spine in the out-of-plane direction. This force opposes the off-planar forces like torsion, twisting and flexing created by the spine and hence serves to stabilize the spine. By reducing such off-planar movements, the disclosed stiffening device of this disclosure increases stabilization of the patient's spine or other body parts in place during the post-operative period.

Turning now to greater detail on the illustrative embodiment shown in FIG. 1, lumbar vertebrae are about 3 centimeters long, (centimeter or "cm" is a metric unit of length) and a stiffener in this situation, spanning two vertebrae, may be about 3 cm long or a little longer. The stiffener, to match this anatomy, may thus be about 1.5 to 2 cm wide, if a single stiffener is used, and about 3 cm long, or a little longer. Other dimensions may be used based on factors such as the subject patient being treated, the spinal segment involved, the procedure performed, and the like. In one embodiment, the stiffener diameter may be several millimeters, up to and including dimensions over 1 cm thick. In other embodiments, thicker or less thick stiffeners may be used, depending on the degree of stiffness desired and the material used for the stiffener. In longer constructs spanning several vertebrae, the stiffeners may be of variable stiffness or a single stiffener may be constructed to have variable stiffness along its course. One potential advantage of this is to have a less stiff construct at the ends of the fused section so as to reduce stress on the adjacent, un-fused, vertebrae.

In this embodiment, each of the two out-of-plane stiffeners 114 is equipped with a stiffener body 116 and two interfaces 118 for joining with connecting rods 110 of the U-shaped legs 108. The stiffener bodies 116 in this embodiment are in a form of a hollow cylinder, having a cross-section of a circle. Other embodiments may have other cross sections, including solid or hollow bodies, such as a solid circle, a hollow square or rectangle, or a solid square or rectangle, a hollow or solid oval shape, and so forth. In this embodiment, the stiffener body 116 tapers to form an interface 118. The interface 118 has a J-shape or hook shape for connecting to the U-shaped legs 108. Other interfaces may be used.

The U-shaped legs 108 include a horizontal portion or connecting rod 110 and lengths or vertical portions 111 that lead to the interface 112 on either side of the leg pair. The length 111 of the legs 108 is the feature that mounts the stiffener 114 out of a plane formed by the fusion rods. Note that in many instances, the fusion rods are bent by the orthopedic surgeon who implants them into the patient. In all these cases, describing the structure of the fusion rods and their location as "planar" is clearly an approximation and the terms "planar" and "plane" are intended as approximations, rather than adhering to strict geometrical terms. The same approximations also hold for other terms taken from geometry in describing the components of the orthopedic stiffening device and the orthopedic fixation device. In embodiments without fusion rods, an approximation of a plane may be a top surface of the pedicle screws or other reasonable approximation of a plane. The stiffener is placed out of this plane, e.g., posteriorly to the plane.

The stiffener and associated components described herein are believed to be effective in preventing the rods from bending in the sagittal plane (a vertical plane bisecting the body front-to-back) and in the coronal plane (a perpendicular vertical plane bisecting the body side to side). The ability to prevent bending in the sagittal plane is expected to be effective in treating lordosis/kyphosis bends of the spine.

Figure 2:
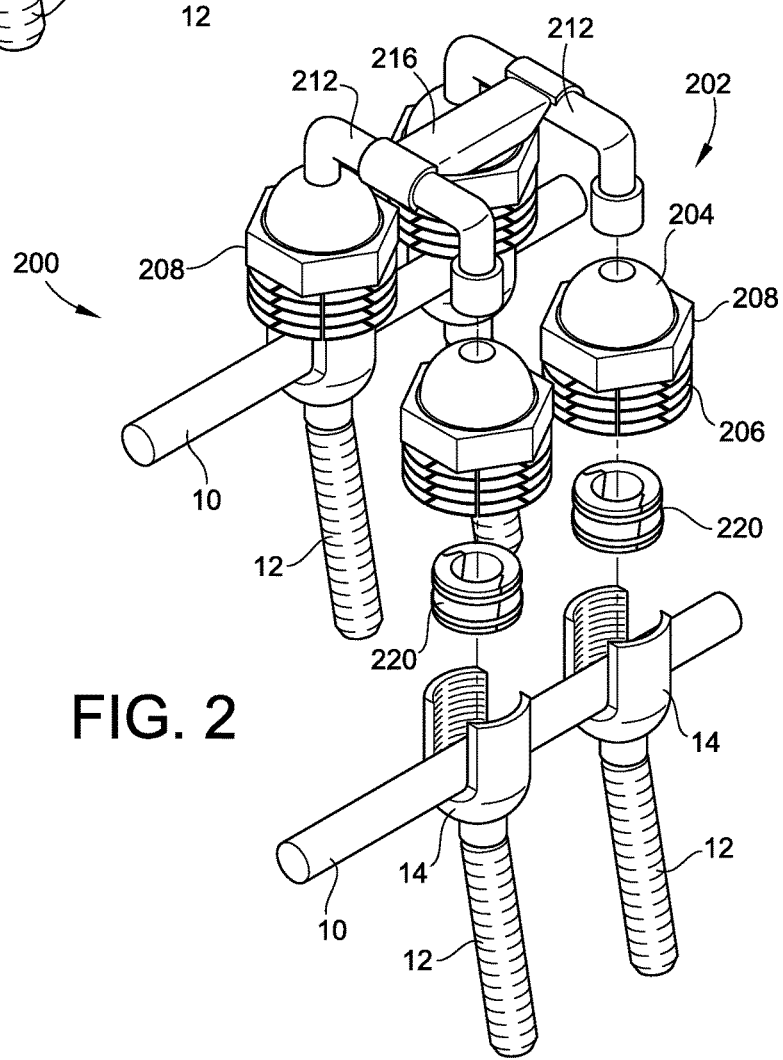
FIG. 2 is a simplified view of a second embodiment of an orthopedic stiffening device with different connectors.

In the embodiment of FIG. 2, an orthopedic stiffening device 200 includes a stiffener 216 and legs 212 similar to stiffener 116 and leg 108, shown in FIG. 1, but this embodiment uses only a single stiffener. In addition, different hardware is used to connect the stiffener 216 and legs 212 to the pedicle screw upper mounting portion 14. The legs 212 are secured to a collet-style adapter 220 for placement into the pedicle screw upper mounting portion 14. An adapter is any thing that adapts two or more things to be fitted together to work together. One skilled in the art will appreciate that alternative adapters may be used for adapter 220.

Figure 3A:
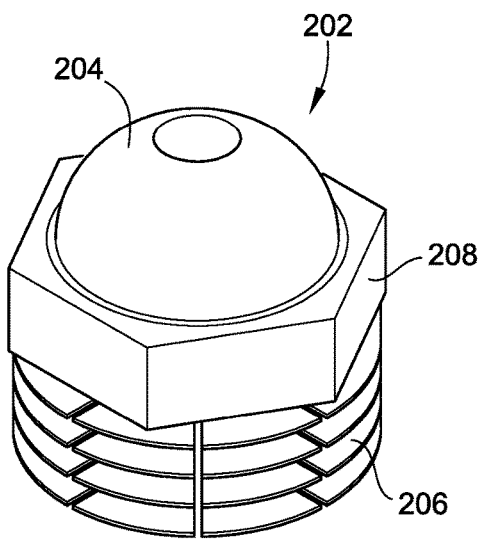
FIGS. 3A and 3B present views of a connector useful for securing a stiffener to an orthopedic fixation device.
Figure 3B:
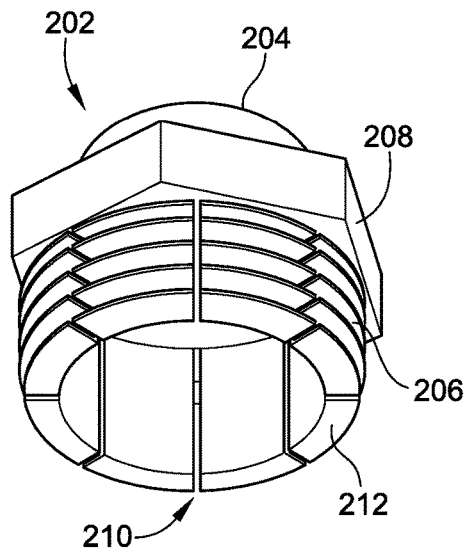

The collet-style adapter 220 is an inner place-holder that secures the legs 212 to the upper portion of the pedicle screws and also prevents crushing of the upper portion when secured in place via collet-style connector 202. Illustratively, the connectors 202 include a connector body 204 and a nut 208 for compressing the body 204 onto the top or mounting portion of the pedicle screw. A connector is any thing that links two or more things together. One skilled in the art will appreciate that alternative connectors may be used for connector 202. As seen more clearly in FIGS. 3A and 3B, the outer surface of connector body 204 has a slight outward taper and external threads 206 to match the internal threads (not shown) of tightening nut 208. Collet body 204 may have gaps 210 to allow for easier expansion and contraction when the nut is loosened and tightened. Interior 212 may be featureless, save for gaps 210, or may have a coarse surface to improve gripping. Threads may or may not be needed on the interior. Collet body 204 is held in place by tightening nut 208 and thus compressing the interior 212 of the collet body 204 onto the upper portion 14 of the pedicle screw.

Figure 4:
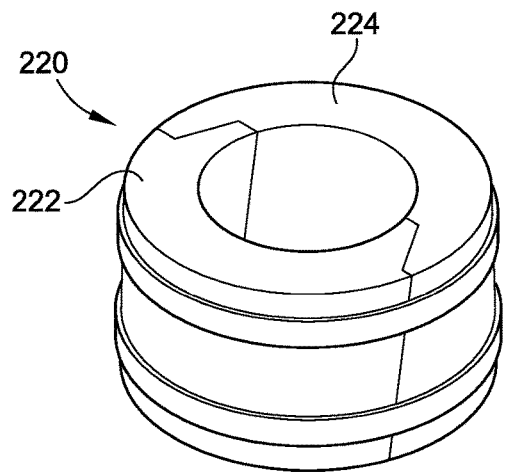
FIG. 4 is a collet-style collar or component useful for mounting legs of a stiffener to an orthopedic fixation device.

As seen in FIG. 4, adapter 220 includes two halves, female half 222 and male half 224. When joined together around leg 212 of FIG. 2, the adapter 220 secures the leg 212 into the upper portion 14 of the pedicle screws. Interface or adapter 220 may take any other useful form, it is simply used to allow the orthopedic surgeon to confidently mount the legs 212 to the pedicle screws without danger of disengagement. Instead of an adapter, the legs themselves could be made of a larger diameter to engage upper portion 14. Using interface or adapter 220 may allow the surgeon to vary the placement of the leg within the pedicle screw, i.e., provide a way to vary the length of engagement, depending on the strength of the grip between the leg, the interface and the upper portion of the pedicle screw.

The out-of-plane orthopedic stiffening device 200 of FIG. 2 is thus used to mount single stiffener 216 a distance above, or posterior to, the fusion rods 10 and pedicle screws 12, that is to say, when viewed by a doctor when operating on the spine of a patient in a prone position. Thus, the stiffener is illustratively located above the "plane" of the orthopedic fixation device, comprising the fusion rods 10 and the pedicle screws 12 and their upper mounting portions 14. It will be appreciated that the stiffener of this disclosure is not limited to "above" the plane. Any off-planar location of the orthopedic fixation device is within the scope of this disclosure.

Figure 5:
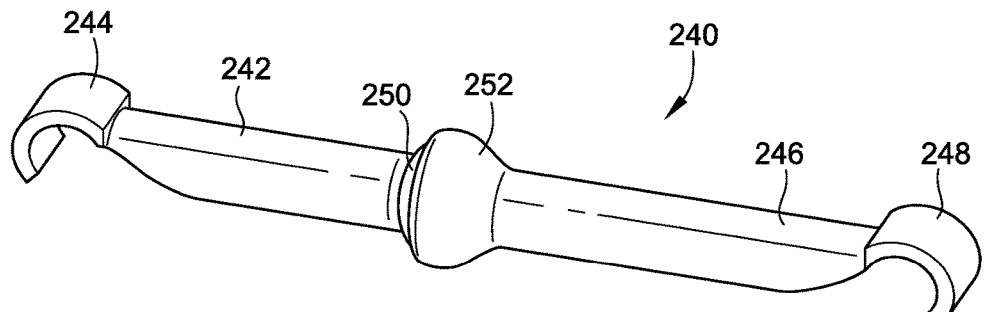
FIG. 5 is a stiffener useful for out-of-plane stiffening of an orthopedic fixation device.

The stiffeners 114, 216 used in the embodiments of FIGS. 1-2 may take the form of the stiffener 240 depicted in FIG. 5, although other embodiments may be used. Stiffener 240 comprises left (e.g., first) and right (e.g., second) portions 242, 246 and left (e.g., first) and (e.g., second) right interfaces 244, 248 for grasping legs of an orthopedic stiffening device for mounting the stiffener out of the plane of an orthopedic fixation device. The left and right interfaces 244, 248 may be hooked as shown for easy connection. Alternatively, connections may be made in any other convenient and effective manner, such as with fasteners, tab-and-slot arrangements, or the like. The left and right portions 242, 246 are joined in the middle or other convenient location along the length of the stiffener. In this embodiment, as illustrated, internal interfaces 250, 252 may be male and female threaded surfaces, so that the length of stiffener 240 may be easily adjusted for a given patient and for a desired result. In other embodiments, the interfaces may allow for adjustment of the angles of the left and right portions with respect to each other, in any direction. As will be discussed below, it may be desirable to adjust the length or angle of the stiffener or stiffeners, or both the length and the angle. This embodiment provides a convenient way to accomplish this. In still other embodiments, the angle of the stiffeners with respect to the legs can be adjusted. In this disclosure, a position of the stiffener with respect to an orthopedic fixation device, such as rods and pedicle screws, denotes an angle of the stiffener with respect to the orthopedic fixation device and may also designate one or more distances of portions of the stiffener from the orthopedic fixation device, i.e., the length of the legs or connectors that fasten the stiffener to the orthopedic fixation devices.

Figure 6A:
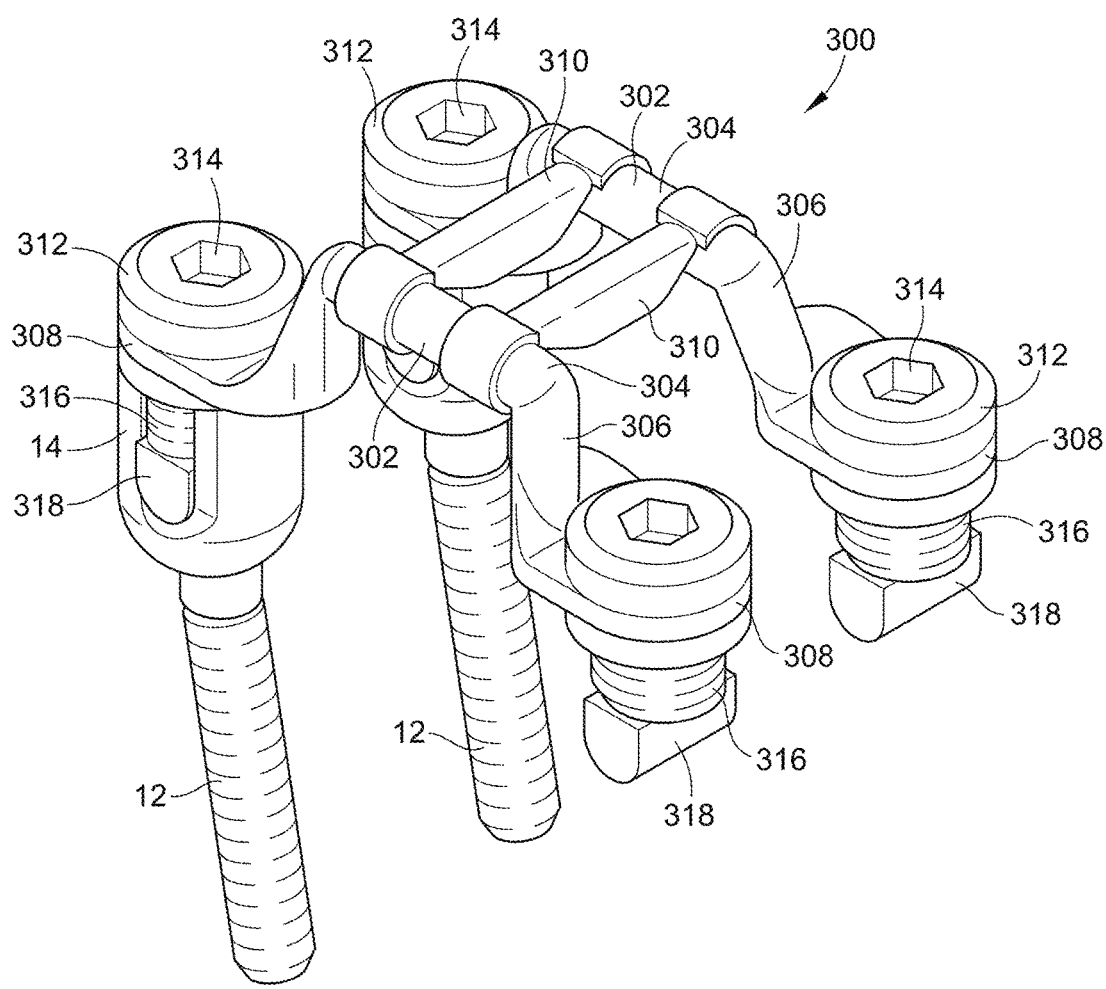
FIGS. 6A-6B depict a simplified view of a third embodiment of an orthopedic stiffening device for placement in a patient, this embodiment suitable for stiffening pedicle screws only, without fusion rods.
Figure 6B:
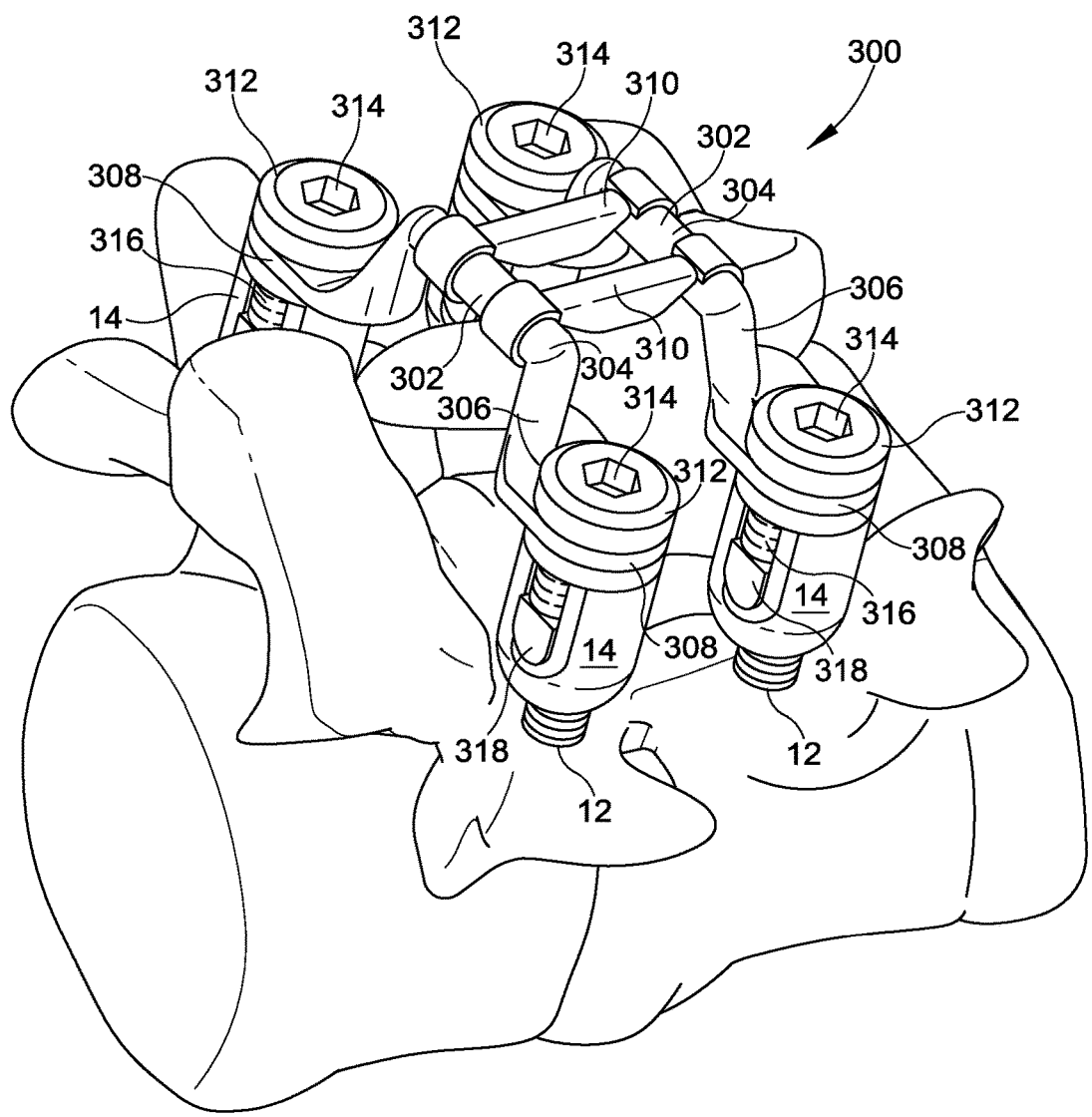

The embodiments discussed above have generally concerned an orthopedic stabilization assembly for use with an orthopedic fixation device that includes fusion rods and pedicle screws, an established orthopedic fixation device. There are other embodiments of an orthopedic stabilization assembly that may be used with other versions of an orthopedic fixation device. An example of a different orthopedic fixation device is one which uses only pedicle screws. An example of such an assembly and the present disclosure is depicted in FIGS. 6A-6B. The orthopedic fixation device in this example comprises only pedicle screws 12 and their upper or mounting portions 14. Normally, mounting portion 14 is used to mount fusion rods, which are not used in this embodiment.

The orthopedic stiffening device 300 in this embodiment includes two pairs of legs 302, two stiffeners 310 and four fasteners 312. Legs 302 may include horizontal portions 304, vertical portions 306 and interfaces 308 for joining to the upper portion 14 of pedicle screw 12. Interfaces 308 may include an orifice or penetration or the interface may be a prong-type interface for ease of connection. Stiffeners 310 may be similar to the stiffeners discussed above. The fasteners 312 provide the connection between the legs 302 and the pedicle screws 12, in this embodiment of the orthopedic fixation device. The device is intended for placement in the spine of the patient, as shown in FIG. 6B.

In this embodiment, there are no fusion rods, so the space in the pedicle screw upper portion that is normally occupied by the fusion rods is filled by special adapters 318 of the fasteners 312. The fasteners 312 also include external threads 316 for engagement with internal threads (not shown) of the upper portion 14 of the pedicle screws 12. This embodiment uses socket heads with an interface 314 for tightening the fasteners, e.g., by a hex wrench or suitable driver. In this embodiment, the stiffening device 300 and pedicle screws 12 act together to stabilize the spine. The fasteners may also be two-part, including a socket-type head that is reversibly connected to a shaped adapter bottom portion 318, the connection made, for example, by a threaded connection or other suitable connection (not shown). In this embodiment, the bottom portion 318 is able to freely rotate independently of the top portion 314. This may also be helpful in assembling the fasteners 312 to the legs 302. The stiffeners are not limited to the two cylindrical stiffeners depicted in FIG. 3. The stiffener or stiffeners may have any suitable shape, such as a shape having a single rectangular cross-section, i.e., a generally planar shape.

Figure 6C:
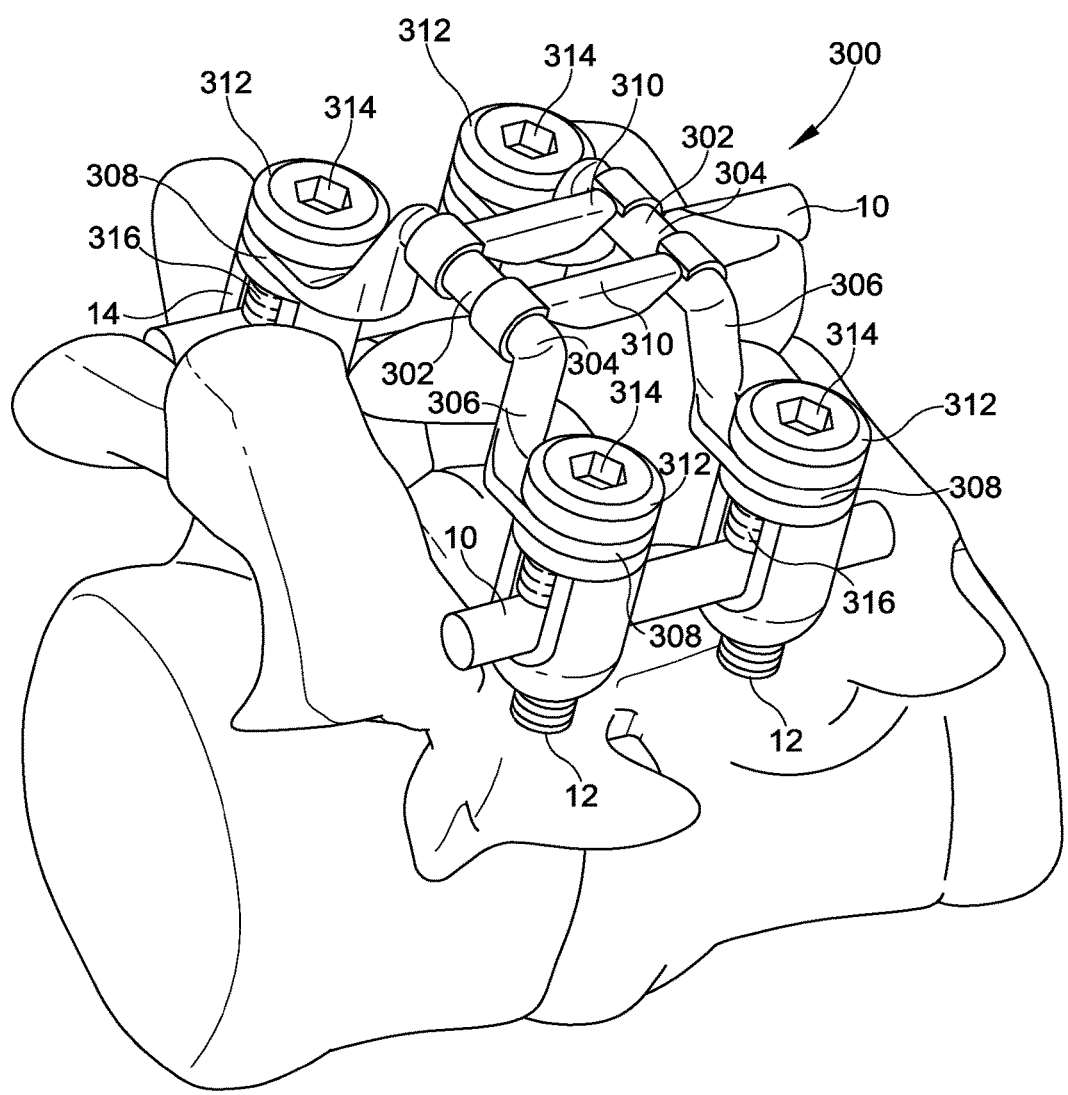
FIG. 6C depicts a fourth embodiment of an orthopedic stiffening device, similar to FIGS. 6A-6B, this embodiment adapted for the use of fusion rods.

In yet another embodiment depicted in FIG. 6C, the same stiffener assembly is used with pedicle screws 12 and fusion rods 10. This embodiment takes advantage of the additional structure provided by fusion rods 10 in correcting the patient's spine. In this alternative embodiment, adapters 318 are no longer needed to secure fasteners 312 to the top portion of the pedicle screws 12. Thus, standard fasteners 312, shown here with convenient socket heads 314 for fastening, are used with fusion rods 10. In this arrangement, the orthopedic stiffening device is arranged to be positioned on a patient's prepared spine in such a manner that pedicle screws 12 can be screwed through interfaces 308 into the corresponding pedicles of the patient.

In the embodiments of FIGS. 1-3, the stiffness of the orthopedic stiffening device may be tailored in several ways. The area of the stiffener may be varied, as well as its thickness. The distance of the stiffener from the spine or other portion of the patient may be varied. This distance contributes to the moment of the area of the stiffener with respect to its distance from an axis, e.g. an axis of the patient's spine or other area which is being treated or straightened. This distance also contributes to the second moment of the area, also known as the "area moment of inertia". Without limiting the present disclosure, these properties are believed to be important in providing additional stiffness and in aiding in the treatment of the patient for whom curvature of the spine or other body parts is needed. The concept is borrowed from mechanical devices, with the legs and stiffeners forming a truss or scaffolding, acting to prevent movement of the truss or scaffolding, as well as the underlying structure of the patient, e.g., the patient's spine as well as the fusion rods and screws.

Figure 7:
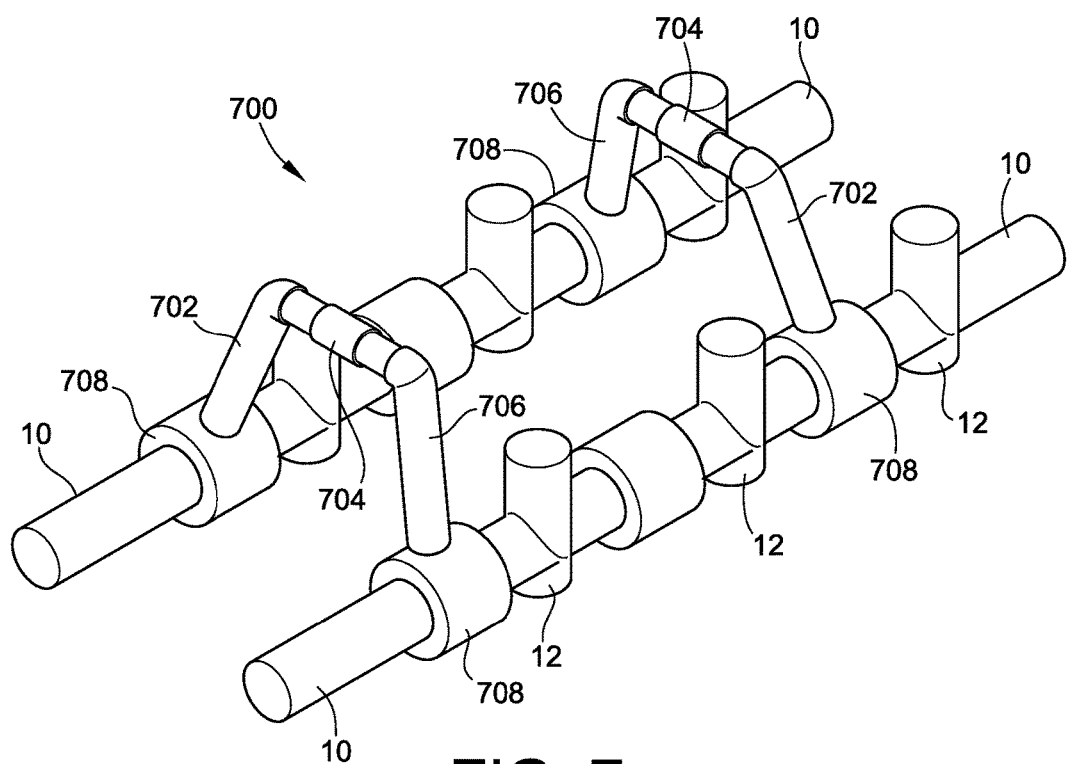
FIG. 7 is a simplified perspective view of an orthopedic fixation device with legs of an orthopedic stiffening device.
Figure 8:
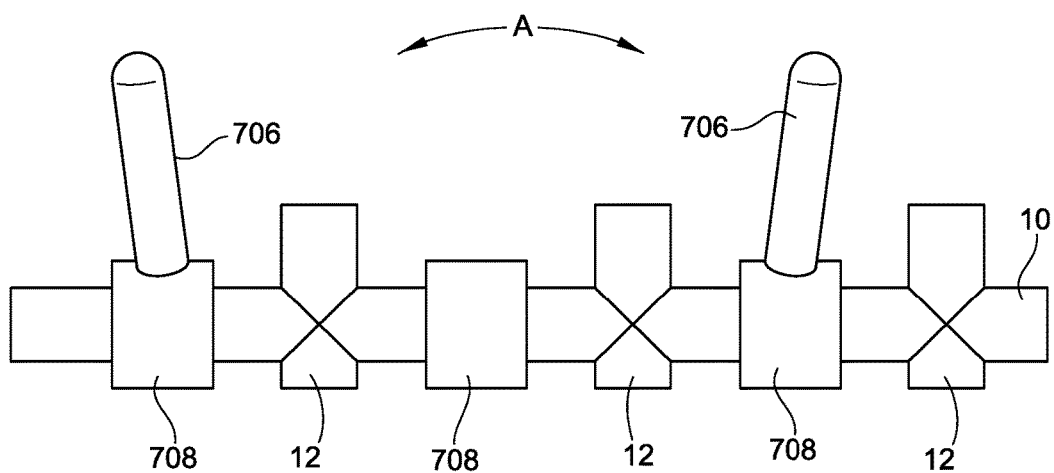
FIG. 8 presents a side view of the embodiment of FIG. 7.
Figure 9:
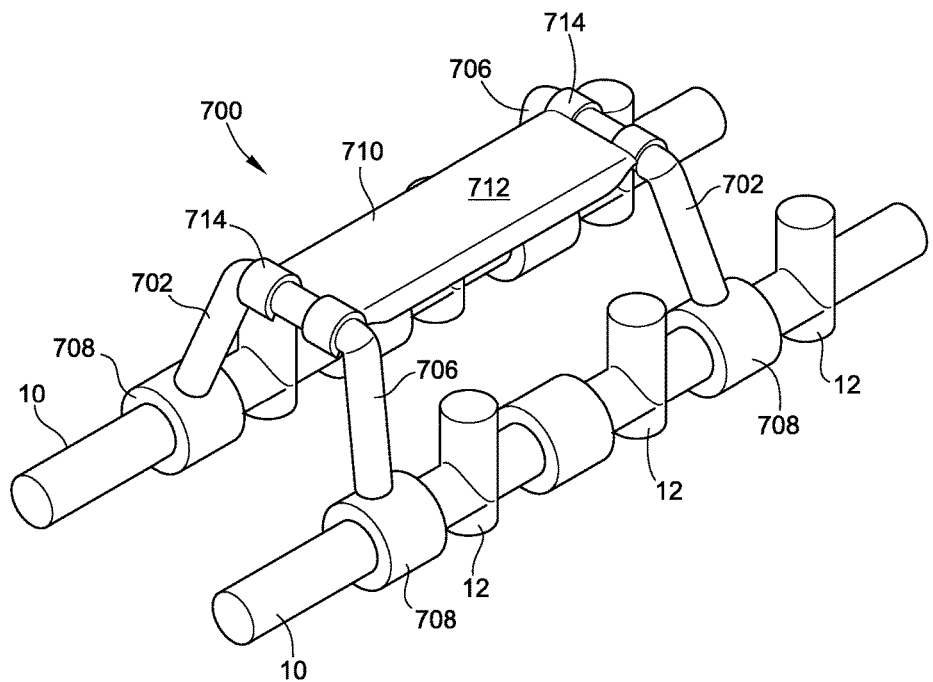
FIG. 9 presents a perspective view of the embodiment of FIGS. 7-8, with a stiffener added.
Figure 10:
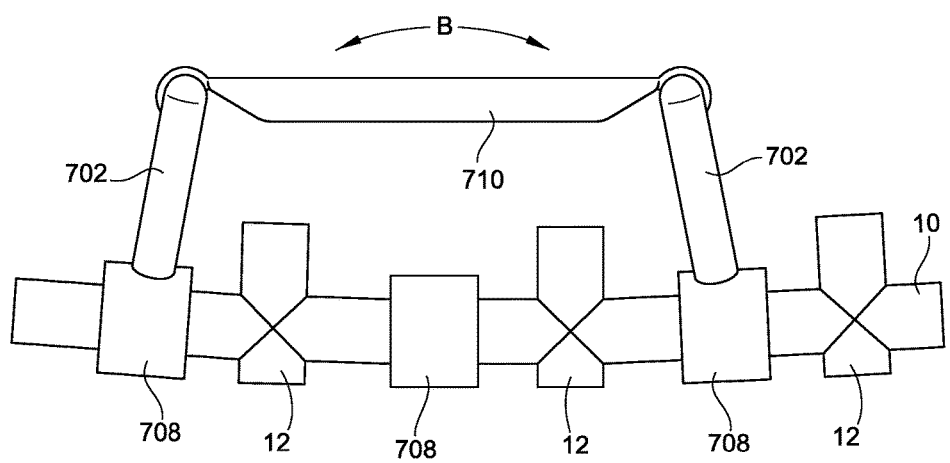
FIG. 10 presents a side view of FIG. 9.
Figure 11:
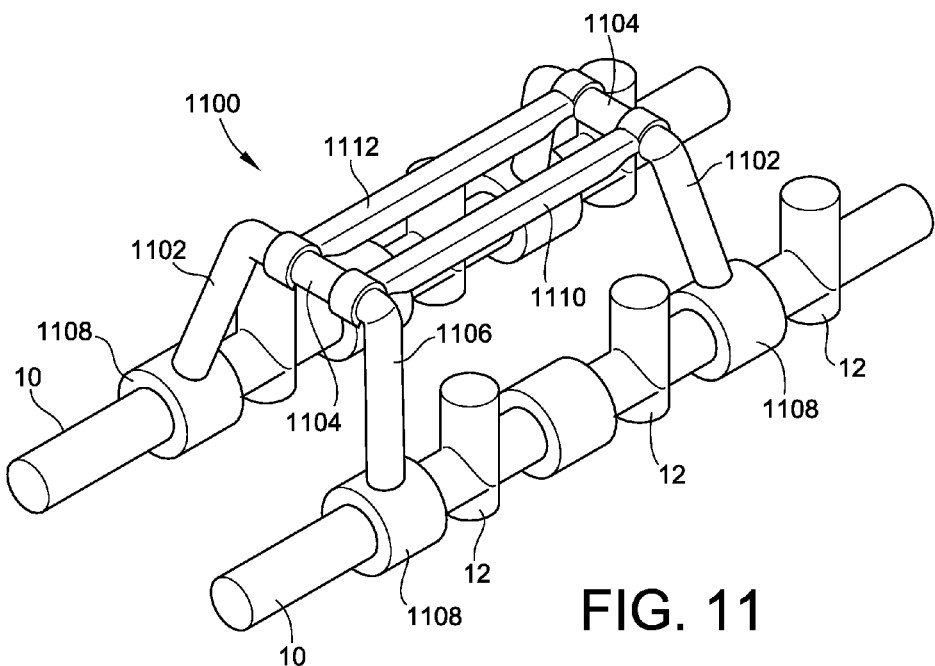
FIG. 11 presents a perspective view of an alternative embodiment of the device of FIG. 9.
Figure 12:
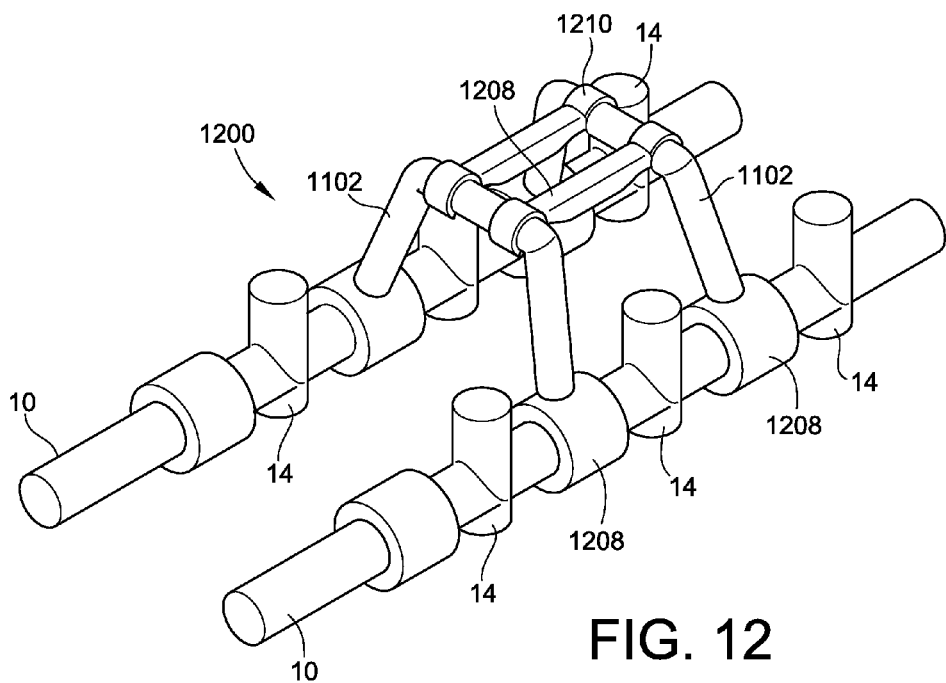
FIG. 12 presents an alternative embodiment of an orthopedic stiffening device of FIG. 11.

FIGS. 7-12 depict additional embodiments of orthopedic stabilization assemblies for out-of-plane stiffening in procedures using orthopedic fixation devices. In these embodiments, the orthopedic stiffening devices are attached to the rods 10 of the orthopedic fixation device. FIGS. 9, 11 and 12 depict devices with differing stiffeners and FIGS. 8 and 10 depict methods for adjusting a lordosis of the orthopedic fixation device and the underlying spine by selecting a distance and an angle or orientation of the legs of the stiffening device as they support and orient the stiffener.

Orthopedic stiffening device 700 is depicted in FIGS. 7-8 in perspective and side views, respectively. The FIG. 7 depicts U-shaped legs 702, each leg having a horizontal portion 704 and a vertical portion 706. The length of the vertical section determines the greatest distance or height that the stiffener can rise above the fusion rods 10. As discussed above, this can have a direct effect on the stiffness that the out-of-plane stiffener imparts to the device and to the orthopedic fixation device.

In this embodiment, U-shaped legs 702 are connected to the fusion rods 10 via feet 708. The feet may simply be as they are depicted in FIGS. 7-10, that is, a hollow horizontal cylinder sufficiently large to fit around the fusion rods, and a vertical or angle-vertical portion for receiving the U-shaped legs 702. The feet may be secured with set screws, also known as grub screws. Additional feet suitable for use in the orthopedic stiffening device are described in greater detail with respect to FIGS. 11 and 13-15. The pedicle screws 12 were described above and are depicted in FIGS. 7-8 only as place-markers. The fusion rods 10 and pedicle screws 12 serve as an orthopedic fixation device in these embodiments. Alternatively, other means for connection may be used in place of the feet.

As shown in FIG. 8, legs and leg vertical portions 706 may be mounted at an angle A to each other. The larger the angle, the less the degree of curvature or lordosis will be imparted by the orthopedic devices. That is, the placement and orientation of the out-of-plane stiffener will affect the treatment that is afforded by the fusion rods and screws to the patient. In general, the additional curvature created is primarily dictated by the distance between the legs versus the length of the stiffener, and may be further manually adjusted in-situ by the surgeon. The surgeon exerts force upwards or downwards on the installed stiffener. Referring to FIGS. 8 and 10, for example, the angles of the legs with respect to the rods may remain fixed, but by installing the stiffener and adjusting or pushing downwardly, the rods are forced to bend further, thereby creating the lordosis.

The completed orthopedic stiffening device 700 is depicted in FIG. 9 with the addition of stiffener 710. Stiffener 710 includes a stiffener body 712 and interfaces 714 for connection to U-shaped legs 702. Stiffener 710 serves the same role in this embodiment that the other stiffeners described above, and described below, serve in their embodiments. The interfaces 714 or other portions of stiffener or plate 714 may be secured using set screws or grub screws, or other convenient and reliable fasteners. In practice, it may be practical to use several sets lengths of stiffeners, such as plate stiffener 710 or rod-configuration stiffeners 114, 240 and 310, for a variety of patients, if possible. This would standardize sizes and be convenient for care institutions, such as hospitals or orthopedic centers, to have standard treatment materials for a variety of patients.

The angle A shown in FIG. 8 is matched with a length of the stiffener 710 in FIG. 9 so that the components of the orthopedic stiffening device will fit together and act for their intended purpose of stabilizing the spine or other portion of a patient. If the components do not fit together as intended, the device may not work as intended for helping with a particular correction for the particular patient. Thus, angle A may be adjusted or a length of the stiffener 710 may be adjusted or selected for the proper fit. The angle may be important to the orthopedic surgeon in his or her prescription for the patient's treatment.

A different angle, for example, is depicted in FIG. 10, angle B determined by legs 702 inclined toward each other. Note that angle B is less than angle A in FIG. 8, angle A determined by legs 702 inclined away from each other. Thus, a prescription for a greater degree of curvature may appear as shown in FIG. 10, while a prescription for a lesser degree of curvature, or lordosis, may appear as the angle shown in FIG. 8. In embodiments, angle B is the orientation angle after the orthopedic fixation device is placed into the patient and after the orthopedic stiffening device is also installed. In some embodiments, an inward facing angle of about sixty (60) degrees to an axis of the fusion rods appears to work well. This angle may also be used to tailor the feet 708 used to attach the legs to the fusion rods. That is, the feet may be designed with a horizontal portion that fits about the fusion rods and an angled vertical portion that orients the legs in a desired manner, such as the desired angle. Other angles may also be used or the surgeon may bend the legs 706 during the operation to fine tune the angle. The feet or collets may also be attached in other manners, such as with grub screws (set screws) or the legs may be joined using the other collets or feet described in this disclosure.

FIGS. 11-12 then depict additional embodiments with different stiffeners and also with different orthopedic stabilization assemblies. In FIG. 11, the orthopedic stiffening device 1100 includes two stiffeners 1110, each having a body 1112 and interfaces or connections 1114 to the legs 1102. The legs 1102 are U-shaped pairs of legs, each pair including a top or horizontal portion 1104 and vertical portions 1106. Legs 1106 connect with feet 1108 for attachment to the fusion rods 10. Feet 1108 have a lower portion for mounting on the fusion rods and an upper portion that is oriented at an inward angle for accommodating the desired angle and lordosis. Feet 1108 are depicted at an angle of about sixty (60) degrees. Other angles may be used. The fusion rods 10 are mounted to the patient via pedicle screws 12 that are mounted to the fusion rods and implanted into the patient.

In the embodiment of FIG. 11, mounting feet 1108 are shown outside pedicle screws 12, suggesting that the orthopedic fixation device spans only two vertebrae of the patient with pedicle screws 12. Normally, there will be a pedicle screw inserted into each vertebra of the patient for the desired area of treatment, so in this case the treatment area and the fixation device are relatively short. The orthopedic stiffening device is longer, since stiffeners 1110 and the feet 1108 include a span that is longer than the two vertebrae into which pedicle screws are inserted. Note that the stiffening device 1100 is not coincident with the orthopedic fixation device. As seen in the figures of this disclosure, the orthopedic stiffening device may be shorter than, longer than, or coincident with the orthopedic fixation device. The feet of the orthopedic fixation device may be mounted on the fusion rods or may instead be mounted to the pedicle screws themselves. They may also be mounted to the ends of the rods, past the outermost pedicle screws and the ends of the rods may be, for example, square in section to enhance the security of attachment of the feet.

In the embodiment of FIG. 12, orthopedic stiffening device 1200 also includes two stiffeners 1210, two U-shaped pairs of legs 1102, which are very similar to those of FIG. 11. In this embodiment, stiffeners 1210 are noticeably shorter than stiffeners 1110 of FIG. 11. The stiffeners 1210 span only about one vertebra with feet 1208, while the orthopedic fixation device spans three vertebrae with pedicle screws 14.

FIGS. 13-18 depict additional embodiments with differing degrees of sophistication for providing out-of-plane stiffening with even greater degrees of freedom for orienting the out-of-plane stiffener and attaching the stiffener to the orthopedic fixation device and even greater precision in its location and orientation with respect to the spine or other portion of the patient.

Figure 13A:
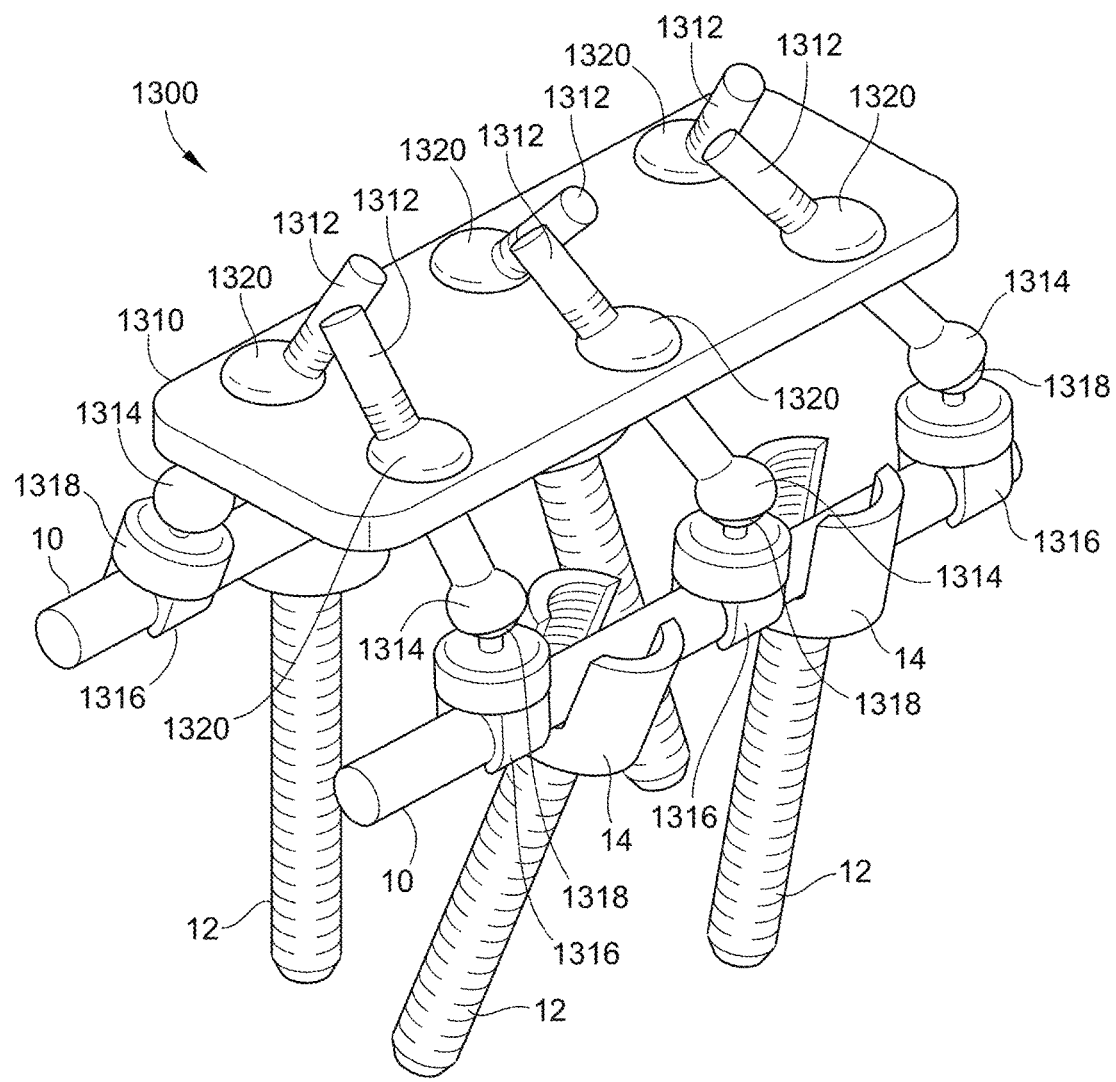
FIGS. 13A-13B depict a simplified view of a single-component out-of-plane stiffener joined to two rods for correcting an orthopedic defect in a patient.
Figure 13B:
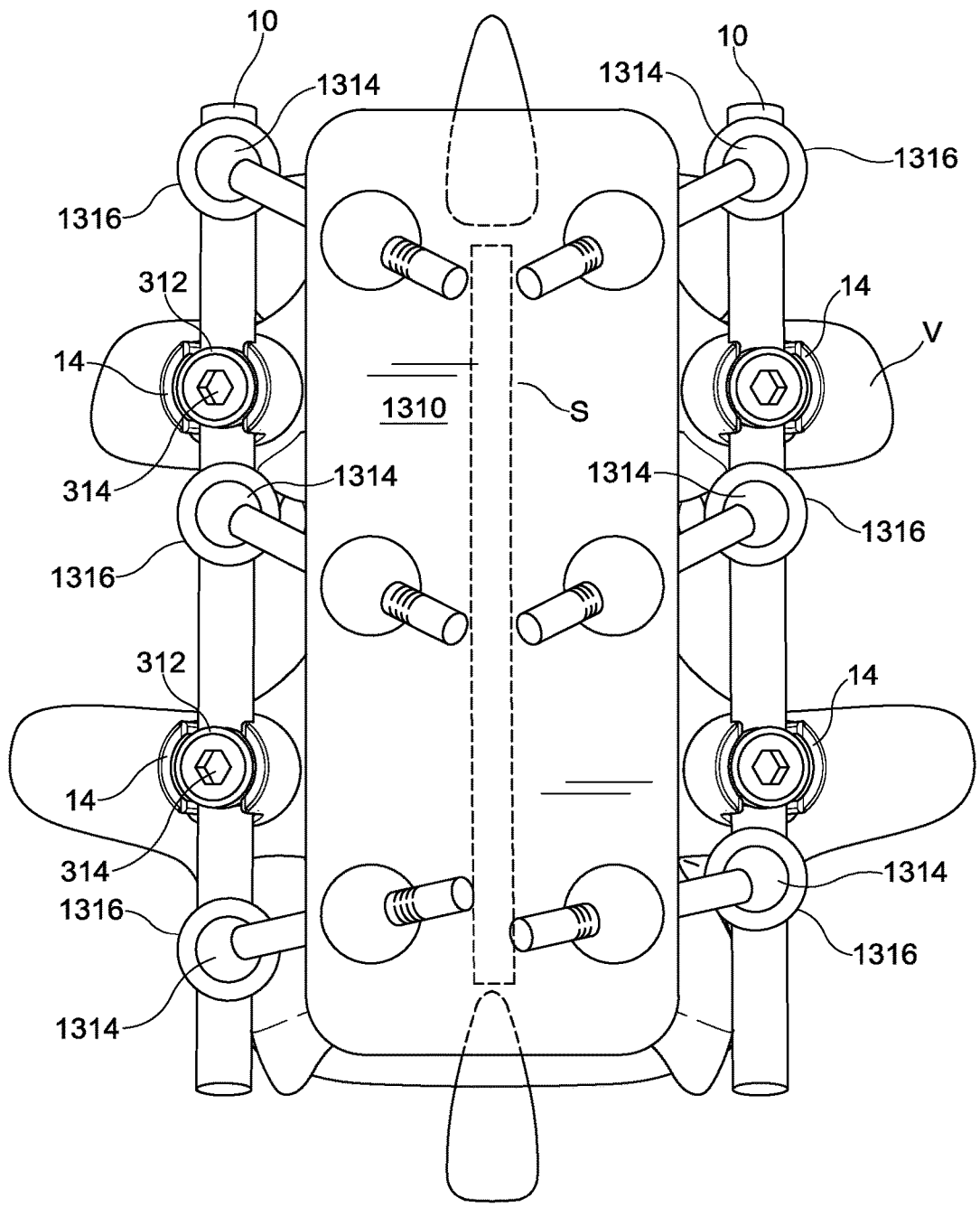

The embodiment of FIGS. 13A-13B is an orthopedic stiffening device 1300, for placement in a patient as shown. As seen in FIG. 13A, this device includes out-of-plane stiffener 1310 and is equipped with six connecting legs 1312, which protrude above and below the stiffener 1310. The connecting legs below the stiffener are joined to the fusion rods 10 via stabilizing feet 1316. In this embodiment, the connecting legs 1312 are joined to the stabilizing feet 1316 via a socket 1314 at the further or distal end of each leg 1312 and a ball 1318 on each foot 1316. In this embodiment, each leg 1312 is mounted securely and fixedly within stiffener 1310 and cannot rotate or otherwise move with respect to the stiffener 1310. Each foot 1316 is mounted securely and fixedly to a fusion rod 10 and cannot rotate or otherwise move with respect to the rod 10. A small amount of movement may be accommodated by the joint formed by the ball 1318 of each foot 1316 and the socket 1314 of each leg. This amount of movement or play should be sufficient for the medical team to install the stiffener 1310 and the legs 1312.

The position and orientation of each leg 1312 is fixed with respect to the stiffener 1310. However, before the legs 1312 are mounted to the stiffener 1310, it is possible to adjust the leg so that the distance from the rod 10 to the stiffener is tailored to the desired dimension. In this embodiment, the legs 1312 themselves have a fixed length, so that they are fully interchangeable among this device or other out-of-plane stiffener devices 1300. By adjusting the position of each leg 1312 with respect to the stiffener 1310, the distance from the stiffener to each fusion rod is fixed, i.e., the length of each leg 1312 is fixed. However, before or after installation, the length of each leg 1312 may be shortened or trimmed, if deemed desirable, and capped, to prevent sharp points that could injure the patient or others.

As noted, the legs 1312 cannot rotate or otherwise move, and the feet 1316 also cannot slide or shimmy along the rods 10. Thus, when stiffener 1310 is installed to stiffen an orthopedic fixation device, the positions of the feet 1316, four points, are fixed, and the distances from the four feet to four points on the stiffener are also fixed. This may be analogous in each plane to four points in a four-point bend system. It may also be analogous to structures for stabilizing bridges, e.g., elevated trusses or arches. In this embodiment, there are no direct connections between the rods 10, e.g., no bars or stiffeners that may be described as "in-the-plane" formed by fusion rods 10. All connections between the rods 10 are made via the stiffener 1310.

As seen in FIG. 13B, orthopedic stiffening device 1300 is intended for installation in a patient's spine, in this case with the pedicle screws 12 embedded in a patient's vertebrae V. Pedicle screws 12 are secured to the rods 10 with fasteners 312. In this instance, a partial laminectomy has been performed on the patient and the patient's spinal cord S is partially exposed. The stiffener 1310 acts as a protective cover over the exposed portion.

The stiffener and associated components described herein are believed to be effective in preventing the rods from bending in the sagittal plane (a vertical plane bisecting the body front-to-back) and in the coronal plane (a perpendicular vertical plane bisecting the body side to side). The ability to prevent bending in the sagittal plane is expected to be effective in treating lordosis/kyphosis bends of the spine and also hold the desired curvature in place, e.g., as a lordosis brace.

Figure 14:
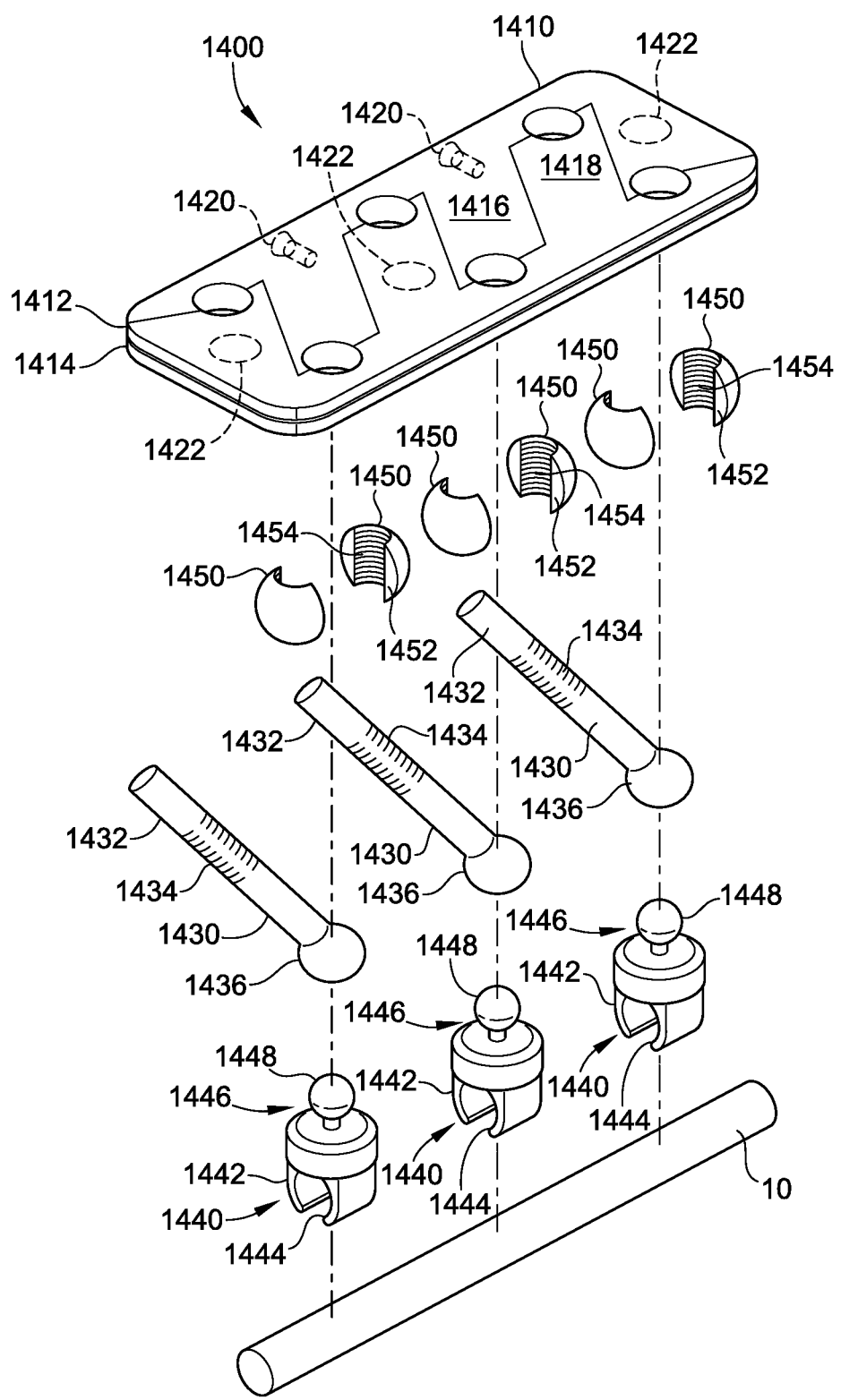
FIG. 14 is an exploded view of a multi-part out-of plane stiffener with additional components used to stiffen an orthopedic fixation device.

Another embodiment of the present disclosure is described with respect to the exploded view of FIG. 14. The embodiment of FIG. 14 is an orthopedic stiffening device 1400 with a stiffener 1410 in the form of a multi-part plate. The multi-part plate 1410 may include an upper portion or half 1412 and a generally identical lower portion or half 1414. Multi-part plate 1410 may be thought of as amenable to modular assembly, with a thickness or tensile modulus (stiffness) tailored to the needs of the patient and the orthopedic surgeons. The top-half 1412 may also include multiple parts, such as left portion 1416 and right portion 1418. The top and bottom halves, or multiple layers, may be joined by counter-sunk or other fasteners 1422 into threaded portions of the other half or other layers, the fasteners oriented in a vertical direction to securely join the layers. The tensile modulus or stiffness of the stiffener may be adjusted by adjusting a thickness of the stiffener or by changing the material used for the stiffener. Left and right halves 1416, 1418 may be joined by similar fasteners and opposite threaded portions in a horizontal clamping direction A, the fasteners entering from a side of the left or right half and having sufficient length to securely join the halves or other portions of each layer, e.g., thirds, quarters, or as desired. The fasteners may be set screws or grub screws, or as desired and convenient.

One difference between the first embodiment of FIG. 13 and the embodiment of FIG. 14 is thus the multi-part nature of the plate or stiffener 1410. One feature of the multi-part plate or stiffener 1410 is that it may be made with cut-outs 1424, 1426 in each half 1416, 1418, the cut-outs depicted in a form of a half-moon. These cut-outs also allow for placement of the connector legs 1430 precisely as the surgeons wish for each patient. This is now explained.

When the stiffener 1410 is assembled, each leg 1430 is joined to the stiffener or plate 1410 with a pivot ball 1450, each pivot ball composed of two halves 1452 with internal threads 1454. The threads are intended to mate with external threads 1434 of the connector legs. Each leg 1430 is threaded into its intended pivot ball 1450 so that the length of leg up to the pivot ball joint is the desired length. This length determines the distance between the fusion rods 1430 and the height of the stiffener 1410 above the fusion rods 10. How this length is determined is explained below.

Connector legs 1430 may be similar to the connector legs 1312 in FIG. 13. Each connector leg 1430 includes an upper portion 1432, a threaded medial portion 1434 having external threads suitable for mating with a pivot ball, and a socket 1436 on its distal end. When assembling the orthopedic stiffening device 1400, the upper portion 1432 may provide a convenient handle. The threaded portion 1434 provides an easy way to adjust the length of the connector leg 1430 that is below the stiffener 1410. The length of engagement of the threads of the connector leg and its respective pivot ball is variable. This length determines the length of leg that remains to connect with its respective foot 1440 on the rod 10. The socket 1436 on the distal end provides a convenient way to join each leg to the feet 1440 provided on the rods 10.

The threads of the connector leg and the pivot ball may be straight threads or tapered threads. With straight threads, there is no limit on the extent of engagement of the threads, save only the length of the threaded portion 1434. As the connector leg is threaded into the pivot ball, the pivot ball accommodates the thread to the full extent of the threaded portion 1434 of the connector leg 1430. If tapered threads are used, there may be limits on the engagement allowed between each leg and its pivot ball, as the tapered portions engage and a limit may be reached. The outline of tapered threads may be thought of as a having a slightly conical shape, while the outline of straight threads has a cylindrical shape. The slightly tapered or conical shape allows for a tighter fit between threaded surfaces, such as for a water-tight or gas-tight fit.

Another feature of tapered threads is that as the threads are engaged, the halves of the pivot ball may be pushed apart, i.e., they may tend to separate, thus tightening the grip of the stiffener halves or portions 1416, 1418 on the pivot balls 1450. With this arrangement, there may be no need for lips or other retaining devices to retain the pivot balls within the stiffener plate 1410. There may be no need for water-tight connection or engagement of the threaded portions, so either tapered or straight threads may be used.

The connector legs 1430 include a socket 1436 at the distal end of the leg. The socket is matched to engage a ball 1448 on foot 1440. The foot 1440, or in this embodiment, six feet 1440, mounts fixedly on the rod 10. Foot 1440 includes a lower portion 1442 or skirt, a clip-on portion 1444 and an upper portion 1446. Upper portion 1446 includes a ball 1448 for pivotal mounting in the socket 1436 of connector leg 1430. The feet 1440 are mounted on the rods 10 near the ends of the rods and at about the midpoint of the stiffening member or stiffener plate 1410. The placement of the left-most four feet 1430 in FIG. 14, the two feet on the far left and at the mid-points, may be thought of as a first four-point bend system, while the placement of the right-most four feet, the two feet on the far right and at the mid-points may be considered a second four-point bend system. With this placement, the series of four-point bend systems helps to make each portion of the stiffener and the rod very rigid.

The gripping members of these systems are the feet. The feet have a clip-on or engagement portion 1444. The feet may be made from any medically acceptable material. Metals may be used, such as chromium-cobalt alloy, titanium alloy, a stainless steel alloy, or the like. The feet may be snap-fit onto the rods by having an effective diameter a suitable amount smaller than the diameter of the rod. Alternatively, retaining features may be used, such as teeth, studs or other protruding members (not shown) suitable for rigidly gripping the rods. The feet may be crimped onto the rods by using an appropriate tool, such as a pliers or clamp, or may be swaged onto the rod through the attachment of upper portion 1446 driving the two parts onto the rod.

A variety of materials medically-acceptable materials may also be used for the other components of the system. The rods, legs and stiffener may all be made of similar metal alloys. Alternative materials may include stiffer plastics or composites, with glass or carbon fiber reinforcements. The stiffener, for example, may be made of PEEK (polyetheretherketone) or other engineering plastic, with or without reinforcement. There are now reinforced technical ceramics, with very high fracture toughness, that may be suitable for these applications. Adding reinforcement allows the user to tailor the strength and modulus, and even to select a desired direction of maximum stiffness of the stiffening plate or member. Further tailoring of the stiffener is accomplished by tailoring the width or thickness of the stiffener. For example, the stiffener may be made as a composite of 2 or 3 layers or laminae, each with a desired stiffness and direction of stiffness. The strength and stiffness of the resulting member is determined by the rule-of-mixtures for plastic or composite materials.

This embodiment discloses multi-part stiffeners. Multi-part stiffeners are useful because they allow tailoring of the dimensions and thus the stiffness of the stiffener. For example, the height dimension, or thickness of the stiffener, may now be made of laminae, or layers, so that the stiffener may be made as thin as needed or as thick as the situation will allow. The stiffness will be governed by the material used, its Young's modulus and its thickness. This gives the medical team additional degrees of freedom in designing a treatment for the patient.

An important part of the present disclosure is a discussion of how and where the feet are placed and how the connector legs and stiffening member are placed. When treatment is prescribed for the patient, such as the use of the rods and pedicle screws, the medical team determines the placement of the rods and the screws. This is done in the conventional manner, seeking the best treatment possible for the patient. The procedure has limits, however, since pedicle screws are typically placed into the vertebrae themselves, and the patient's particular anatomy limits the options for placing the rods. Within these limits, the medical team uses the present disclosure to limit the relative movement of the rods with respect to each other.

Using these criteria, the team decides the most appropriate placement for the stiffening member, such as stiffener plate 1410. The placement of the stiffening member should be accomplished so as to encompass the desired length of the rods. Alternatively, multiple stiffening devices may be used instead for the segment being treated. If the stiffener is to be effective in preventing motion, motion should be prevented to the greatest extent possible over the length of the rods and the extent of the stiffener. Thus, in one embodiment, the feet will be placed towards the ends of the rods or treatment area, and additional feet may be placed at intermediate positions. The exact placement is not thought to be critical since it is the stiffness or rigidity of the resulting connection that is important. Thus, the medical team has a certain amount of freedom or discretion in placing the feet.

In the example of FIG. 14, for instance, the feet have been placed at the ends, and at about the midpoint of stiffening member or stiffener plate 1410. This placement securely grips the stiffening member and provides support for the stiffening member to resist movement of the rods as the patient goes about daily living. Other embodiments for longer rods may use, for example, eight legs, including the end points and the one-third and two-thirds points of the rods or the desired treatment area. This may be considered as a continuing series of four-point bend systems. Multiple stiffening assemblies may also be used independent of each other along the length of a long fusion construct.

Some embodiments may use only four legs or feet. The feet are thus placed in order to provide the greatest resistance to movement of the rods. In one embodiment, the feet may be placed onto the rods before the rods are secured to the patient. In another embodiment, the feet may be placed onto the rods after the rods are secured to the patient. In another embodiment, the feet may comprise two parts and may be assembled on the rods before the rods are secured to the patient, with final assembly or securing of the two parts to each other after the rods are secured to the patient. See additional discussion of more sophisticated feet below.

The placement of the legs is also important, but there is a certain amount of freedom here also. Once the feet have been placed, the position of at least one portion of the legs is fixed, i.e., the bottom portion of the connector legs that attach to the feet. The other degree of freedom is the length of the legs. The legs should be placed so that the stiffening member is roughly parallel to the rods and, in one embodiment, is about 2 cm posterior to the rods. This dimension is not critical and other separation distances may be used. The greater the separation, the greater the stiffness of the orthopedic stiffening device in its location. This is because the distance contributes to the moment of the area of the stiffener, and the second moment of the area, also known as the moment or inertia or second moment of the area, with respect to an axis in the plane of the patient's spine, i.e., the orthopedic fixation device.

Once the position of the feet is decided, the medical team or the surgeon may construct a template, or plan, for the position and placement of the legs. In general, each leg will likely be positioned at an angle to the stiffening member. This is because, given human anatomy, it is unlikely that each leg will fit straight from its foot into its position in the stiffening member in such a way that the stiffener will be roughly parallel to the rods. The template may then be used by the team to select and assemble components for the orthopedic stiffening device.

Once the attachment feet are attached to the rods at locations desired by the surgeon, a template is constructed that indicates the position of the feet. In general, this template is then taken to a separate table where the surgical team can construct the orthopedic stiffening device away from the operation site. In one embodiment, the team may use malleable wire to note the locations of the feet. In other embodiments, the team may use more sophisticated navigation systems to measure and note the location of the feet. Navigational systems comprising navigation platforms for orthopedic navigation empower surgeons to quickly and effectively make data-driven decisions in the operating room with respect to noting the locations of the feet, By integrating the most advanced instrument tracking technologies, intra-operative imaging and surgical planning software, surgical navigation systems allow surgeons to precisely identify the location of the feet in relation to patient anatomy, even as that anatomy is shifting in real-time. The assembled orthopedic stiffening device, with a stiffener and the connecting legs, is then given to the surgeon for installation. In general, only a few adjustments are necessary, tightening the legs and pressing the balls of the feet into the sockets of the legs. In other embodiments, the device may be placed onto the rods, and the feet tightened in place.

The template or plan is used to decide the length of each leg and its orientation or angle with respect to the stiffening member or stiffening plate 1410. Using these lengths and orientations, the team then assembles the stiffening plate 1410, threads the legs 1430 into the pivot balls 1450 and orients each leg into its desired position in the stiffening plate. Note that the stiffening plate 1410 may be made in several parts. As the stiffening member or plate is assembled, the pivot balls and legs may be oriented as desired with a desired length for each leg. Once assembled, a check on the assembly may be made by checking the closeness of the fit for each ball-and-socket joint that will hold the assembly in place. Adjustments may be made before placement is made onto the patient. Note that the assembly of the legs into the plate, including all the steps discussed above, may be done away from the patient once the template or plan has been designed. This allows greater freedom for the medical team and less risk for the patient. The ability to adjust each leg and its length and placement is important. Note that the rods to which the orthopedic stiffening device is attached may be curved or bent to match the anatomy of the patient and the desired result.

Figures 15A, 15B, 15C:
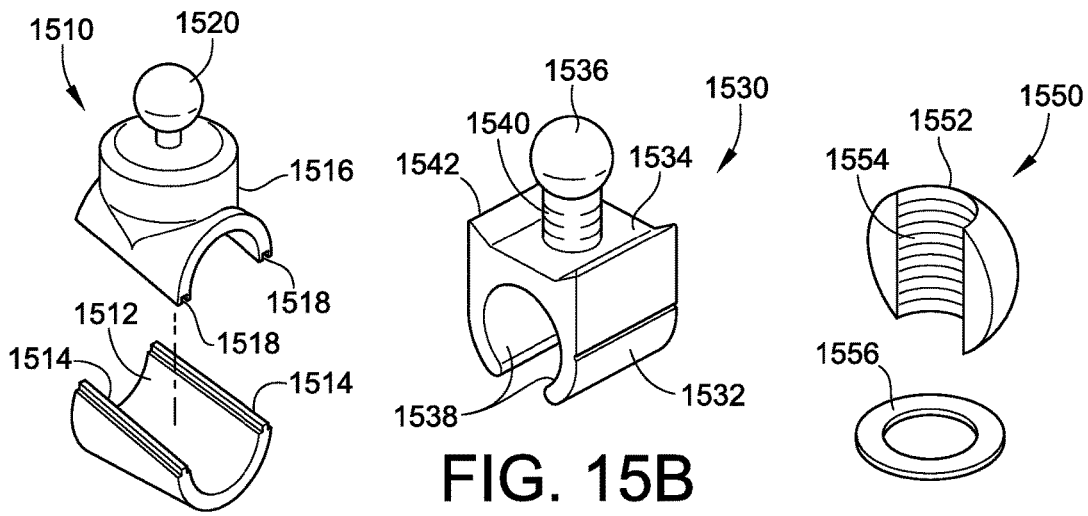
FIGS. 15A, 15B and 15C are perspective views of additional components useful to mount the out-of-plane stiffener of FIG. 14.

In the above discussion of the out-of-plane stiffeners, some embodiments of the connectors are illustrated. These connectors include primarily the feet that secure the legs to the rods and the pivot balls that secure the legs to the out-of-plane stiffener and may apply to other embodiments of the orthopedic stiffening device, e.g., those shown in FIGS. 7-12. FIG. 15A depicts a first embodiment of a foot, a two-part, collet-like foot 1510. Foot 1510 includes a bottom portion 1512 and a top portion 1516. Foot 1510 is intended for placement about a rod, such as the fusion rods 10 discussed above. Top portion 1516 includes a terminal ball 1520, discussed above as providing a connection for a connector leg 1430, as shown in FIG. 14. Top portion 1516 is a general shape of a half-cylinder, with a downward-facing groove 1518 intended to capture an upward-facing tongue 1514 of the bottom portion 1512. The groove may instead be on the bottom and the tongue on the top, as desired and convenient.

The foot may be assembled onto a rod by placing the bottom portion 1512 under the rod, the top portion 1516 atop the rod, and sliding the two together to engage the tongue and groove portions and reduce the internal diameter as the two parts are slid together. The assembly is expected to be a very tight assembly and may be made using pliers or another tool to slide the two components together. The connector may be applied to the end of the rod 10 and allow similar connection to a leg 106 which may enter the connector aligned with the rod 10. This arrangement may be useful for connecting two fused areas or extending the extent of a fusion at subsequent surgery, where the leg 106 or an addition rod 10 are secured to the original rod 10 by means of both sliding into the connector 1510 with or without a connecting ball 1520. The placement of the top portion 1516 and its ball 1520 determine the connecting point to its respective connector leg.

Another foot embodiment is depicted in FIG. 15B. Foot 1530 has a snap-fit or clip-on design and is intended for placement around a rod, such as a fusion rod. Foot 1530 includes a lower gripping portion 1532 and a top mounting portion 1534. Foot 1530 also includes a top-mounted terminal ball 1536 for connecting to its respective connector leg. The foot may also include an outer ridge 1538 and a retaining feature 1542, such as a lip or teeth. The outer ridge or lip may be useful if an installment cap or other device is used to press the foot onto the rod. The cap may be used to hold the foot in place until it is pressed onto the rod in the precisely desired position.

FIG. 15C depicts a pivot ball 1550, and in particular a pivot ball half 1552 with internal threads 1554. The threads should mate with those of a connector leg with which the pivot ball is assembled. The pivot ball may be used in conjunction with a resorbable washer or shim 1556. The washer or shim is designed to resorb into the body and tissue of the patient over time as the orthopedic stiffening device remains within the patient. The idea is that when the device is implanted within the patient, the device should be as rigid and stiff as possible. Later, as the orthopedic correction continues, it may be desirable to allow a little more movement. By resorbing into the body, the fit between the pivot ball and the connector leg loosens. Thus, the fit between the connector leg and the stiffening member also loosens. This allows more freedom of movement for the stiffening member, and thus for the patient, over time. Conventional resorbing materials may be useful for this purpose, such as the materials used for resorbable sutures. Example materials include, without limitation, polyglycolic acid (PGA), polylactic-co-glycolic acid (PLGA), polylactic acid (PLA), poly-L-lactic acid (PLLA), Novosyn, Safil, Vicryl, Vicryl Plus and the like as well as hydroxyapatite or tri-calcium phosphate.

Figure 16:
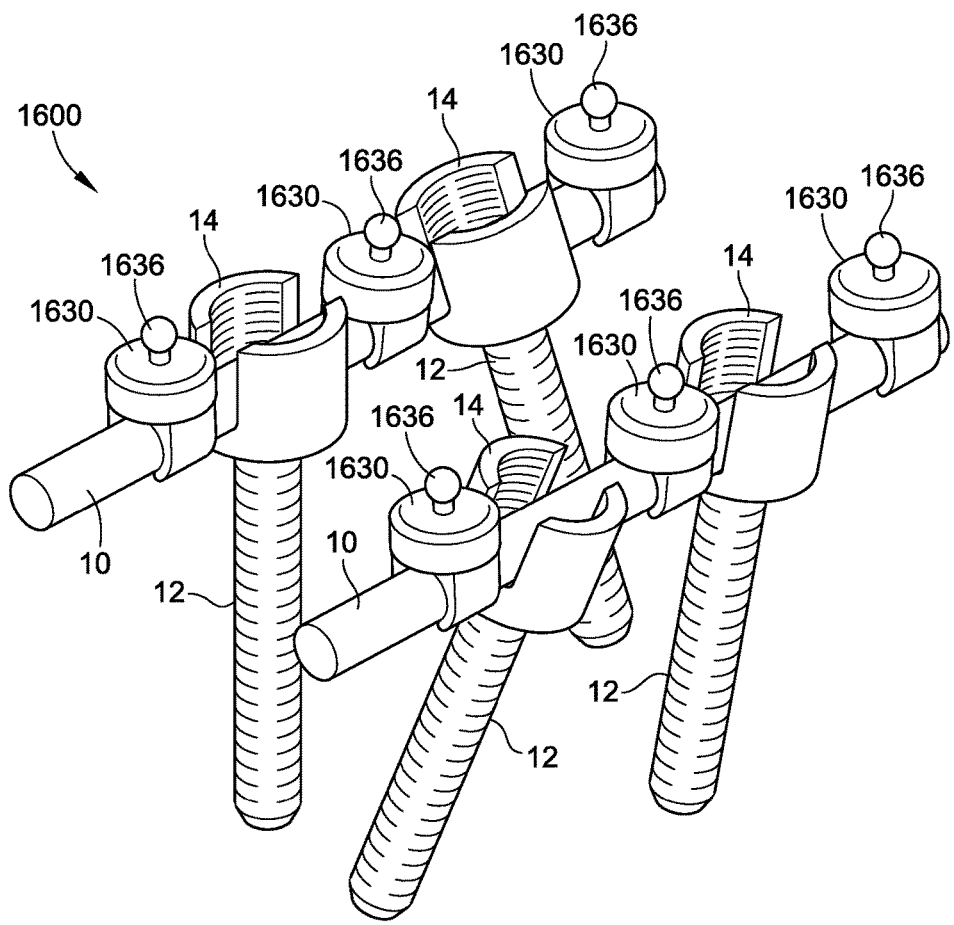
FIG. 16 is perspective view of an orthopedic fixation device with feet in place for mounting an out-of-plane stiffener.
Figure 17:
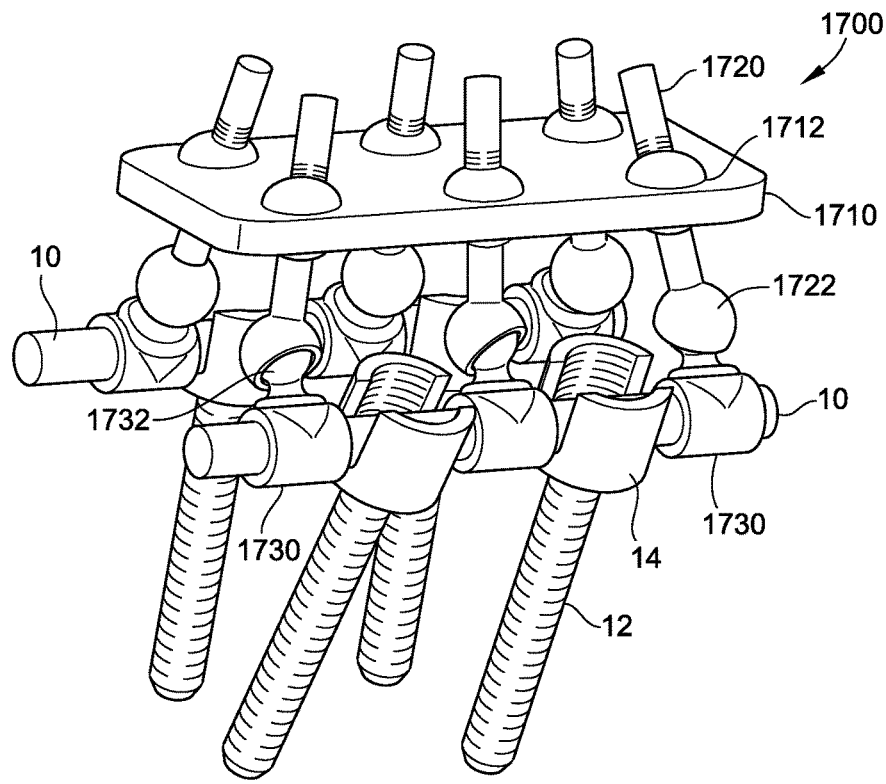
FIG. 17 is a perspective view of an alternate embodiment of an out-of-plane stiffener used with an orthopedic fixation device.

The FIGS. 13-15 depicted a stiffening member and the components useful in a system for helping a patient. FIGS. 16-17 depict more detailed views of the implantation of such systems. FIG. 16 depicts an early stage of implantation, while FIG. 17 depicts a more advanced state of a different embodiment.

In FIG. 16, a perspective view is shown of an implantation site 1600 in which rods 10 and pedicle screws 12 have been implanted into a patient for an orthopedic correction. Mounts or coupling members 14 on the pedicle screws 12 are used to hold the rods 10. In this site, clip-on style feet 1630 have been pressed onto the rods 10. Each foot 1630 includes a terminal ball 1636 for placement into a socket, as discussed above, from a respective connector leg. FIG. 16 thus depicts the site as it will appear when it is time for installation of the stiffening device, including the stiffener and the connector legs.

FIG. 17 depicts the orthopedic stiffening device 1700 as it will appear when the stiffener 1710 has been installed into an orthopedic fixation device to stiffen the assembly. The orthopedic fixation device in this embodiment includes the rods 10, pedicle screws 12 and mounts or coupling members 14 of the pedicle screws, to support the rods. The remainder of the components belongs to the orthopedic stiffening device. In this embodiment, collet-style feet 1730 have been installed onto the rods. As seen in the figure, the feet are oriented in somewhat differing directions, i.e., the terminal balls 1732 of the feet are not oriented straight up or vertically.

The feet 1730 are two-part feet and may be installed with any desired orientation, although it will be expected that the terminal ball will generally be oriented in an upward direction, if only for convenience in joining the connector legs 1720 and their sockets 1722 to the balls 1732 of the feet. In this embodiment, the upper portions of the connector legs, the portions of the legs above the stiffener 1710, are seen to be oriented at different angles. Since the legs in at least this embodiment are straight, the figure demonstrates the versatile nature of the stiffener, the legs and the pivot balls. The legs may be placed in any orientation allowed by the ball-and-socket joint at the one end and the pivot ball in the center portion.

Once placed in this orientation, each ball-and-socket joint has a small amount of freedom of movement, but each joint is also constrained by the other five legs and their constraints. Thus, while the stiffener may be considered to be a reinforcing or stabilizing truss, each leg may also be considered a strut or a truss component that contributes to the stiffness and stability of the structure. It should also be noted that the great flexibility or variability of the legs allows the surgeons many options for placement and orientation of the stiffener 1710. The stiffener is desirably parallel to the rods and also to the patient's spine, or other body structure for which treatment has been prescribed. With the ability to twist and orient the legs, and with the freedom allowed by both the ball-and-socket joints at the feet, and the pivot balls at the plate or stiffener, the surgeon has a great deal of flexibility. While the stiffener is desirably parallel, the stiffener will work as well when held in a non-parallel orientation. When implanted properly, it will still be stiff and will resist body movements no matter whether it is off-axis by 5 degrees or more. It will be stiff and will resist bending movements, flexing, twisting and so forth.

Figure 18:
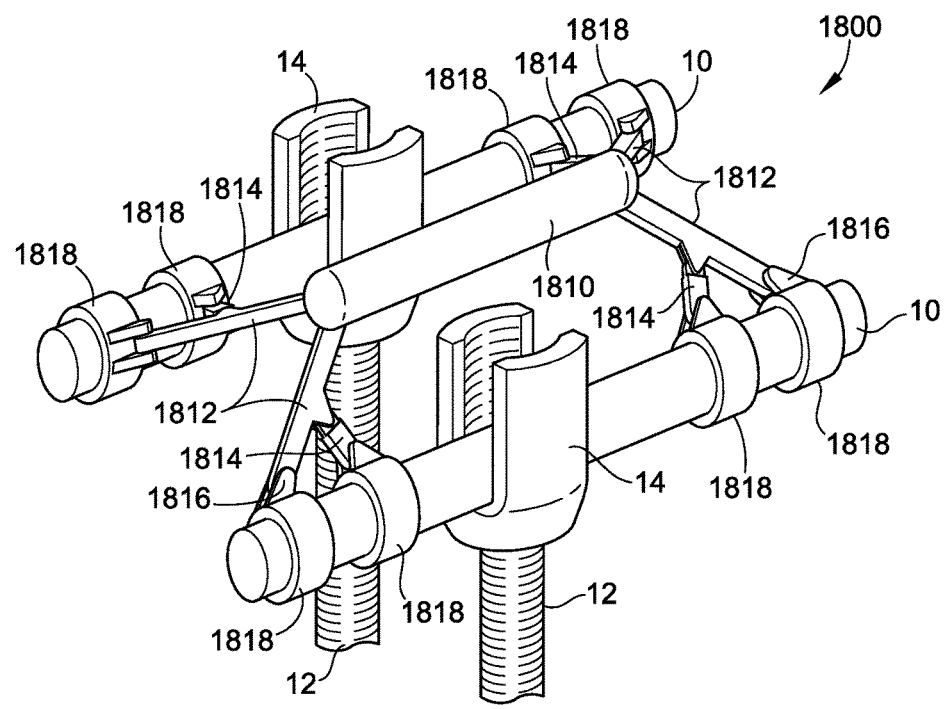
FIG. 18 is a perspective view of another alternate embodiment of an out-of-plane stiffener.

Another embodiment is depicted in FIG. 18. Orthopedic stiffening device 1800 includes a stiffener 1810 that is not in the form of a plate, but a solid cylinder or a bar. In this embodiment, stiffening bar 1810 is anchored to fusion rods 10 via four legs 1812 and four pivoting connectors 1814, 1816. In one embodiment, the legs 1812 are fixedly attached to the bar 1810. In other embodiments, as shown in FIG. 18, the legs may be pivotally attached to the bar, for example by mounting short axles or pivot points near the ends of the bar and mounting the legs to the axles through orifices in the ends of the legs 1812 (these details not shown).

Each of the legs and pivoting connectors is held fast to the rods 10 via double feet or double pivoting collars 1818. These feet or collars 1818 may be similar to the feet 1510, 1530 discussed above, or they may take the form shown as a double collar, as shown. The inner diameter of the collars is only slightly greater than the outer diameter of the fusion rods 10. This makes the collars lock in place when they are attached to the rod. The collars or feet may be brought close together to lock them in place and thus prevent movement of the collars, and thus the rods, to provide increased compression to the stiffening bar and increased tension to the rods. Note the four-point loading in this environment also. Stiffener 1810 is connected to the remainder of the orthopedic stiffening device 1800 via the four legs 1812. In one embodiment, the feet 1818 may be fixed in place, in any suitable manner, such as the methods described above. The feet 1818 may be brought closer together or moved apart, to change their positions and the position of the stiffener 1810 by pliers or other suitable tool. The feet may also be secured in place with set screws or other suitable retainers or fasteners.

As noted, the loading on the stiffener may be increased by moving the feet further apart, which also provides increased tension to the bars. This is an enhanced way to apply a corrective force to the patient without the need to remove the rod and screws, so long as the forces and the positions of the rods and screws can tolerate the added force. For example, one may wish to create a lordotic (inward) bend of the patient's lumbar region. With the device disclosed herein, the desired deflection of the rods may be estimated. The template of desired distances may be calculated, and the required lengths of the legs then determined. When the stiffener is installed, this force is then applied to the rods. This is especially easy to achieve in the embodiment of FIG. 18, in which the movement of the feet, after the stiffener is installed, determines the load on the stiffener and on the rods. This imposition of force may also be achieved with the other embodiments, since the snap-on feet may be moved to their snap-on positions later in the process. The collet-type feet may also be used to impose loads on the stiffener and on the rods. This task is made far easier with the disclosed out-of-plane stiffener that is not only much stiffer, but easy to design for each patient and relatively easy to install, pre-loaded for the intended orthopedic correction. Moving the feet and sending the device into this loaded state is roughly equivalent to imposing the angle discussed with respect to FIG. 10, where a curvature or lordosis is imposed to help correct the patient's spine.

Other embodiments of the present disclosure may also include a kit for an orthopedic stabilization assembly. The kit may include a stiffener as discussed above, and may also include a plurality of legs for connecting to an orthopedic fixation device. In one embodiment, the legs include a first portion for connecting to the stiffener and a second portion for connecting to the orthopedic fixation device. The kit may include packaging that maintains the components in a sterile condition until the kit is needed for a patient. Some embodiments of the kit may include feet or other connectors for connecting the legs to the orthopedic fixation device. Some embodiments may include a plurality of rods, as described above, and a plurality of pedicle screws. For example, some kits may include two lengths of rods, of a suitable diameter to act as fusion rods. The kit may also include a plurality of pedicle screws and a corresponding number of feet for attachment to the rods. Other kits may include other components as described above.

In other embodiments, the present disclosure may be used for orthopedic correction of other body parts, such as a cranio-facial, mandible or pelvic orthopedic correction that is needed. Thus, cranio-facial procedures may attempt jaw repairs, for example, as a relatively common procedure. A stiffener according to the present disclosure may be used to fix the relative positions of other parts of the skeletal system such as the cranium, mandible, sacrum, ribs, sternum, clavicle, scapula, humerus, ulna, radius, carpels, metacarpels, phalanges, coxa, iliu, ischium or pubis.

The embodiments and figures discussed herein have generally concerned parallel rods and corresponding pedicle screws. The stiffener is generally secured to the rods with legs arranged in corresponding rows on both sides of the stiffener or reinforcing member. In some embodiments, the legs attached to the rod on one side also attach to the reinforcing member on that side, i.e., all the legs are attached in an ipsilateral manner. In some embodiments, it may be desired for spacing or therapeutic reasons, to attach one or more legs from one side to the opposite side of the reinforcing member. That is, one or more legs may be attached to the reinforcing member in a contralateral manner. All these are within the scope of the present disclosure.

In view of this disclosure, it will be seen that technologies are generally described for out-of-plane, posterior stiffening for orthopedic stabilization and correction devices. An orthopedic stiffening device for attachment to an orthopedic fixation device is disclosed. The orthopedic fixation device typically includes a plurality of corrective rods, such as fusion rods, and pedicle screws. The pedicle screws are implanted into the pedicles of vertebrae of a patient and the fusion rods are attached to the screws by mounting devices or coupling members. The orthopedic stiffening device disclosed herein includes a stiffener that acts in a plane apart from a plane occupied by the fusion rods. The components typically include a stiffener and legs, and may include attachment devices, such as feet or the pivot balls discussed above. The feet are attached to the rods, the feet suitable for placement of a plurality of legs for connecting a stiffener. The stiffener, such as a plate or a bar, acts as a truss and does not allow separate movement of the fusion rods. In one embodiment, the fusion rods connect to each other only through the stiffener member, with no direct connections between the rods. That is, no additional ties or bars are needed to stiffen the rods and hold them in place for the orthopedic correction.

A basic embodiment of an orthopedic fixation device includes two rods, such as fusion rods, secured to the patient in a conventional manner, such as by pedicle screws. An orthopedic stiffening device is then used to prevent or limit movement of the orthopedic fixation device. A stiffener is attached with at least four points, using feet as points of attachment for legs that connect to the stiffener. The attachments themselves need not be as rigid as possible, because the number of legs and feet limit the degrees of freedom, and thus movement, of the stiffener as well as the movement of the rods. This same embodiment may use additional legs to impart additional stiffness. However, in many patients, fusion rods to accommodate two vertebrae may only be about 3-4 cm long, and it may be difficult to attach four feet and connector legs to this relatively short length. The use of four points provides a four-point rigid system to resist bending and flexure when the patient moves about. Other orthopedic fixation devices may use only pedicle screws for attachment to the patient. These devices may also be stiffened and made more effective by the present disclosure.

A more complicated embodiment may include longer rods in an attempt to bridge more vertebrae, e.g., 3, 4, or more vertebrae. In these embodiments, the fusion rods may be 6-10 cm long and may be joined to the patient by 6 or more pedicle screws. The desire is still the same, to stiffen the orthopedic fixation device by making it as stiff and strong as possible. Accordingly, additional legs may be used, for example 6 or 8 legs. In the example of FIGS. 13 and 17, six legs and six connecting feet are used. The first 4 legs may be considered a first four-point system, while the middle 2 legs and the remaining 2 legs may be considered as a joined, second four-point bend resistant member. Many other embodiments and variations are easily imagined by those with skill in the art.

The devices disclosed herein, and methods of their use are adaptable to a very large number of positions and rod contours that make the stiffeners suitable for any portion of the spine, not restricting these devices and methods to the lumbar region, but also to thoracic and cervical portions as well. In addition, the method may be suitable for hip corrections, and other portions of the body, such as pelvic, facial and cranial treatment.

The stiffener works in a complex manner to prevent bending, twisting and rotation between the rods. However, this complexity is transparent to the medical team and the surgeon placing the device into the patient. As noted, the device uses only a few components and uses them in an advantageous way for a simple and yet very effective installation.

The out-of-plane stiffeners of this disclosure provide stiffening effects in a plane that is different from the plane defined by two or more rods or by some portion of the pedicle screws for embodiments of an orthopedic fixation device that does not use fusion rods. The plane defined by the two or more rods has been previously explained. Hence, the out-of-plane stiffeners of this disclosure advantageously introduce off-planar forces for use in fixing two or more rods with respect to each other. These off-planar forces are different from and additional to the planar forces that are introduced by conventional stiffeners, such as cross-connectors. More specifically, the out-of-plane stiffeners advantageously introduce one or more vertical stress components of force for use in stabilizing the orthopedic fixation device. The one or more vertical stress component of force are useful in keeping the rods from off-planar movements with respect to each other. Such off-planar movements include torsion, twisting and flexing. By reducing such off-planar movements, the disclosed stiffening device of this disclosure increases stabilization of the patient's spine or other body parts in place during the post-operative period.

The present disclosure recognizes the multi-plane nature of the orthopedic problem. The design solution opens a new domain for compact and effective stiffening of orthopedic fixation devices. In particular, the off-plane or out-of-plane nature of the stiffener means that it is more secure in stabilizing the lordotic curve of the spine in the lumbar segment, a key aspect of the nature of such surgery. In addition, the stiffener plates disclosed here may act as a protective barrier to the exposed spinal canal after the surgeon removes the spinous processes to reach the affected area of the vertebrae or to relieve spinal canal stenosis.

The disclosure is simple in design and easy to use. The configuration of the stiffening device creates the out-of-plane area moment of inertia with respect to the orthopedic fixation device. This out-of-plane area moment of inertia illustratively makes the stiffener more resistant to bending due to residual forces that may increase in the stiffener as the area moment of inertia is acting against the deformation of the bone. Each leg is configured to adjust the out-of-plane area moment of inertia of the stiffener with respect to the orthopedic fixation device. In the illustrative example shown in FIGS. 9-12, for example, the stiffening device including stiffening member and legs may be configured in the shape of an arch. For example, the arch may be configured so that the legs impart an inward or compressive force. Hence, attachment of such a stiffener device to the rods may cause the rods to be pulled together into a tight fit. As the rods are pulled together the stiffener may itself be bending and becoming stiffer to further bending. In other words, the increased residual forces in the stiffening member resist the out of plane moments imparted by the adjustment. The right adjustment by a caregiver may provide an appropriate adjustment of the rods that both fixes and stabilizes their position with respect to each other. Alternatively, the arch may be configured so that the legs impart an outward or tensile force. Hence, attachment of such a stiffener device to the rods may cause the rods to be pulled apart. As the rods are pulled together the stiffener may itself be bending and becoming stiffer to further separation. In other words, the increased residual forces in the stiffening member resist the out of plane moments imparted by the adjustment.

It will be appreciated from this disclosure that the stiffener device of this disclosure may be configured to provide these and other forces to an orthopedic fixation device. One skilled in the art will appreciate from this disclosure that the stiffener including the shape of the stiffener member and the legs can be configured to deliver any type of off-planar force. Indeed, some of the residual force opposing the out of plane moments imparted by the adjustment may even be provided by the legs which are making the adjustment. One skilled in the art will also appreciate from this disclosure that the residual stiffness of the stiffener member (and adjustment legs of the stiffener device, if the legs are designed to provide residual stiffness in operation of the stiffener device) can be tuned to reach the desired outcome. The shape of the stiffener device including shape of the stiffener member and the legs are a matter of design choice.

As explained above, the out-of-plane area moment of inertia illustratively makes the stiffener of this disclosure more resistant to bending due to residual forces that may increase in the stiffener as the area moment of inertia is acting against the deformation of the skeletal portion or spine. This stiffening helps to bring the deformed portion into alignment and to hold the deformed portion in alignment following an operation.

A further benefit is that the stiffener may act as an incision guide if and when additional or corrective surgery becomes necessary. This means that making a dissection down to the dura may be less hazardous to the patient. In addition, the apparatus and techniques discussed herein are applicable to both open surgery and minimally invasive surgery (MIS) procedures.

The present disclosure uses a better approach to the large forces at work in the body that tend to distort present orthopedic fixation devices once they are placed into the body. Using a kinematic mindset, the stiffeners described herein, and the improved method of securing the stiffeners, offers much greater resistance to movement and shape changes inside the body after implantation. Thus, the desired shape of the device as it is implanted is subject to much less change than prior art devices. The corrective orthopedic device with the stiffener disclosed herein is thus much more likely to achieve the desired effect, or correction, on the patient's spine or other portion of the patient's anatomy.

Technologies generally described herein are intended for out-of-plane orthopedic stiffening devices. When applied to spinal procedures, these devices are primarily intended for posterior mounting. However, these devices are not limited only to orthopedic (skeletal) procedures such as spinal procedures, and may be used in other corrective procedures. These may include facial and cranial reconstruction procedures. The very light and yet very rigid structure or scaffold that results from the use of this disclosure allows its application in a variety of situations. Applied to facial procedures, the use of the disclosed out-of-plane stiffener will likely be applied anteriorly, although it is not limited to this orientation. Application may also be made to pelvic and cranial procedures.

One embodiment of the present disclosure is an orthopedic stiffening device. The orthopedic stiffening device includes a stiffener configured for out-of-plane placement with respect to an orthopedic fixation device and a plurality of legs, each leg including a first portion being configured to connect to the orthopedic fixation device and a second portion configured to connect to the stiffener, wherein each leg is configured to adjust a position of the stiffener with respect to the orthopedic fixation device. In some embodiments, the orthopedic fixation device comprises screws configured for securing to a vertebra. In some embodiments, the orthopedic fixation device comprises pedicle screws. In some embodiments, the orthopedic fixation device further comprises a plurality of rods. In some embodiments, the stiffener is configured to provide an out-of-plane area moment of inertia of the stiffener with respect to the orthopedic fixation device.

In some embodiments, the stiffener comprises at least one plate or one cylinder connected to the plurality of legs. In some embodiments, the plurality of legs includes at least one pair of legs. In some embodiments, the orthopedic stiffening device further includes a plurality of connectors for joining the plurality of legs to the orthopedic fixation device. In some embodiments, the connectors include a plurality of tapered collets, each tapered collet adapted for receiving a leg of the plurality of legs and securing the leg to a pedicle screw of the orthopedic fixation device. In some embodiments, the orthopedic stiffening device further includes a plurality of feet for attachment to the rods, each foot of the plurality of feet comprising an end connector defining a first part of a ball and socket connection, wherein each leg of the plurality of legs comprises an end connector defining a second part of the ball and the socket for attaching the plurality of legs to the plurality of feet, the first part and the second part configured to attach together to each other in a ball and socket arrangement.

In some embodiments, each foot of the plurality of feet is adapted to connect to the rods via a compression fit or a collet-type tongue and groove fit. In some embodiments, the stiffener is selected from the group consisting of a generally planar plate, a plurality of generally planar plates, a generally cylindrical stiffener and a plurality of generally cylindrical stiffeners. In some embodiments, the stiffener comprises a multi-part generally planar plate. In some embodiments, the orthopedic stiffening device is adapted to allow adjustment of an angle of the legs with respect to the stiffener and to allow adjustment of an angle of the legs with respect to the orthopedic fixation device. In one embodiment adapted to allow adjustment of the angle, the angles are suitable for adjusting a lordosis of the skeletal system of the patient when the orthopedic stiffening device is attached to the orthopedic fixation device and the orthopedic fixation device is attached to the patient. In some embodiments, the orthopedic stiffening device of any one of the above is provided in a kit that further includes the orthopedic fixation device.

In another embodiment, the orthopedic stiffening device includes a stiffener; and a plurality of legs, each leg including a first portion configured to connect to an orthopedic fixation device, the orthopedic fixation device intended for implantation into a skeletal portion of a patient, and a second portion configured to connect to the stiffener, wherein the stiffener is configured to provide an out-of-plane area moment of inertia, thereby making the orthopedic fixation device and the skeletal portion of the patient more resistant to bending than the orthopedic fixation device and the skeletal portion of the patient without the stiffener, and wherein each leg is configured to adjust a position of the stiffener with respect to the orthopedic fixation device.

In some embodiments, the orthopedic fixation device is selected from the group consisting of a plurality of rods, screws, or combination thereof. In some embodiments, the stiffener is selected from the group consisting of a generally planar plate, a plurality of generally planar plates, a generally cylindrical stiffener and a plurality of generally cylindrical stiffeners. In some embodiments, the stiffener comprises a generally planar plate defining a plurality of openings therethrough for connecting the plurality of legs to the plate and further comprising a plurality of pivot balls, one for each of the plurality of legs, for connecting the plurality of legs to the plate. In one embodiment, an outer surface of each leg of the plurality of legs comprises a threaded engagement surface for connection with an inner threaded surface of each of the plurality of pivot balls. In some embodiments, the orthopedic stiffening device further includes a plurality of feet, at least one foot for each leg, for attaching the legs to the orthopedic fixation device.

In one embodiment, the plurality of feet are adapted for attachment to a plurality of fusion rods of the orthopedic fixation device. In one embodiment, each leg of the plurality of legs comprises an end connector defining one part of a ball and a socket for attaching the plurality of legs to the plurality of feet, each foot of the plurality of feet comprising an end connector defining a second part of the ball and the socket, the first part and the second part configured to attach together to each other in a ball and socket arrangement. In some embodiments, the plurality of legs includes at least one pair of legs joined together at or near the second portion. In one embodiment, a length of the stiffener is adapted for adjusting an angle of the two connected pairs of legs to each other, the angle suitable for adjusting a lordosis of the skeletal system of the patient. In some embodiments, the orthopedic stiffening device further includes a plurality of connectors between the plurality of legs and the orthopedic fixation device, each connector comprising a tapered collet for capturing a leg and securing the leg to a pedicle screw of the orthopedic fixation device.

Another embodiment of the present disclosure is a method of stabilizing a skeletal system of a patient. The method includes steps of attaching a plurality of legs to a stiffener and securing the stiffener to an orthopedic fixation device using the plurality of legs, the stiffener being secured in a plane apart from the orthopedic fixation device, wherein the stiffener provides adjustable off-planar loading to the orthopedic fixation device to make the orthopedic fixation device and the skeletal portion of the patient more resistant to bending than the orthopedic fixation device and the skeletal portion of the patient without the stiffener. In one embodiment, the method includes a step of adjusting a length of at least one leg. In some embodiments, the orthopedic fixation device is selected from the group consisting of a plurality of rods, screws, or combination thereof. In some embodiments, the stiffener includes a stabilizing plate and the stabilizing plate and plurality of legs act to stiffen the orthopedic fixation device.

In some embodiments, a stiffness of the stiffener and the plurality of legs with respect to the skeletal system of the patient is adjustable by varying a distance between the stiffener and the skeletal system of the patient. In some embodiments, there is an additional step of securing the legs to the orthopedic fixation device with a plurality of feet. In some embodiments, there is an additional step of adjusting an angle of the legs with respect to the stiffener or to the orthopedic fixation device. In methods of using this additional step, adjusting an angle of the legs with respect to the orthopedic fixation device is effective to adjust a lordosis of the skeletal system.

Another embodiment of the present disclosure is a method of stabilizing a skeletal system of a patient. The method includes steps of placing a plurality of connecting feet onto an orthopedic fixation device, attaching a plurality of legs to an orthopedic stiffener configured to provide an area moment of inertia and connecting the orthopedic stiffener to the plurality of connecting feet using the plurality of legs. The method also includes steps of securing the orthopedic stiffener in a plane apart from the skeletal system of the patient and adjusting the plurality of legs to adjust off-planar loading to the orthopedic fixation device to make the orthopedic fixation device and the skeletal portion of the patient more resistant to bending than the orthopedic fixation device and the skeletal portion of the patient without the stiffener.

In one embodiment, there is an additional step of tightening the plurality of legs into the stiffener using a corresponding plurality of pivot balls. In some embodiments, the stiffener occupies a fixed plane posterior to the orthopedic fixation device. In some embodiments, adjusting the plurality of legs changes the length of the legs or angle of the legs with respect to the stiffener, the orthopedic fixation device, or both. In some embodiments, the method includes adjusting a lordosis of the skeletal system of the patient by adjusting an angle of the legs with respect to the orthopedic fixation device. In some embodiments, the stiffener is selected from the group consisting of generally planar plate, a plurality of generally planar plates, a generally cylindrical body and a plurality of generally cylindrical bodies.

In some embodiments, the method is adapted for posterior spinal fusion for vertebrae selected from the group consisting of lumbar, thoracic and cervical vertebrae. In some embodiments, the method includes adjusting a stiffness of the device for preventing movement of the orthopedic fixation device by adjusting a modulus of the stiffener or by replacing the stiffener. In some embodiments, the method includes adjusting a position or an orientation of the legs or the stiffener.

Another embodiment is a kit for stabilizing an orthopedic fixation device. The kit includes a stiffener configured for out-of-plane placement with respect to the orthopedic fixation device, a plurality of legs, each leg including a first portion being configured to connect to the orthopedic fixation device and a second portion configured to connect to the stiffener, wherein each leg is configured to adjust a position of the stiffener with respect to the orthopedic fixation device, and packaging for holding the stiffener and the plurality of legs and maintaining the stiffener and the plurality of legs in a sterile condition prior to use.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An orthopedic stiffening device comprising:
a stiffener configured for out-of-plane placement with respect to an orthopedic fixation device, wherein the orthopedic fixation device comprises a plurality of pedicle screws configured for securing the orthopedic fixation device to a vertebra and a plurality of rods;
a plurality of legs, wherein each leg of the plurality of legs includes a first portion configured to connect to the orthopedic fixation device and a second portion configured to connect to the stiffener,
wherein each leg of the plurality of legs is configured to adjust a distance of the stiffener from the orthopedic fixation device; and a plurality of connectors for joining the plurality of legs to the orthopedic fixation device, wherein the plurality of connectors comprises a plurality of tapered collets, wherein each tapered collet of the plurality of tapered collets is adapted for receiving a leg of the plurality of legs and securing the leg of the plurality of legs to a pedicle screw of the plurality of pedicle screws.

2. The orthopedic stiffening device of claim 1, wherein the orthopedic stiffening device is adapted to allow adjustment of an angle of one or more legs of the plurality of legs with respect to the stiffener and to allow adjustment of an angle of one or more legs of the plurality of legs with respect to the orthopedic fixation device.

3. The orthopedic stiffening device of claim 2, wherein the angle is suitable for adjusting a lordosis of the skeletal system of the patient when the orthopedic stiffening device is attached to the orthopedic fixation device and the orthopedic fixation device is attached to the patient.

4. The orthopedic stiffening device of claim 1, wherein the stiffener is configured to provide an out-of-plane area moment of inertia of the stiffener with respect to the orthopedic fixation device.

5. The orthopedic stiffening device of claim 1, wherein the stiffener comprises at least one plate or one cylinder connected to the plurality of legs.

6. The orthopedic stiffening device of claim 1, wherein the plurality of legs includes at least one pair of U-shaped legs.

7. The orthopedic stiffening device of claim 1, wherein the stiffener is selected from the group consisting of a generally planar plate, a plurality of generally planar plates, a generally cylindrical stiffener, and a plurality of generally cylindrical stiffeners.

8. The orthopedic stiffening device of claim 1, wherein the stiffener comprises a multi-part generally planar plate.

9. The orthopedic stiffening device of claim 1, further comprising a kit including the orthopedic fixation device.

10. A method of stabilizing a skeletal system of a patient, comprising:
placing a plurality of connectors onto an orthopedic fixation device, wherein the orthopedic fixation device comprises a plurality of pedicle screws for securing the orthopedic fixation device to a vertebra and a plurality of rods;
attaching a plurality of legs to an orthopedic stiffener configured to provide an area moment of inertia;
connecting the orthopedic stiffener to the plurality of connectors using the plurality of legs, wherein the plurality of connectors comprises a plurality of tapered collets, wherein each tapered collet of the plurality of tapered collets is adapted for receiving a leg of the plurality of legs and securing the leg of the plurality of legs to a pedicle screw of the plurality of pedicle screws;
securing the orthopedic stiffener in a plane apart from the skeletal system of the patient; and
adjusting the plurality of legs to adjust off-planar loading to the orthopedic fixation device to make the orthopedic fixation device and the skeletal portion of the patient more resistant to bending than the orthopedic fixation device and the skeletal portion of the patient without the stiffener.

11. The method of claim 10, wherein the stiffener occupies a fixed plane posterior to the orthopedic fixation device.

12. The method of claim 10, wherein adjusting the plurality of legs changes the length of one or more legs of the plurality of legs or angle of one or more legs of the plurality of legs with respect to the stiffener, the orthopedic fixation device, or both.

13. The method of claim 10, further comprising adjusting a lordosis of the skeletal system of the patient by adjusting an angle of one or more legs of the plurality of legs with respect to the orthopedic fixation device.

14. The method of claim 10, wherein the stiffener is selected from the group consisting of a generally planar plate, a plurality of generally planar plates, a generally cylindrical body and a plurality of generally cylindrical bodies.

15. The method of claim 10, wherein the method is adapted for posterior spinal fusion for vertebrae selected from the group consisting of lumbar, thoracic, and cervical vertebrae.

16. The method of claim 10, further comprising adjusting a stiffness of the device for preventing movement of the orthopedic fixation device by adjusting a modulus of the stiffener or by replacing the stiffener.

17. The method of claim 10, further comprising adjusting a position or an orientation of one or more legs of the plurality of legs or the stiffener.

18. A kit for stabilizing an orthopedic fixation device, the kit comprising:
a stiffener configured for out-of-plane placement with respect to the orthopedic fixation device, wherein the orthopedic fixation device comprises a plurality of pedicle screws configured for securing the orthopedic fixation device to a vertebra and a plurality of rods;
a plurality of legs, wherein each leg of the plurality of legs includes a first portion configured to connect to the orthopedic fixation device and a second portion configured to connect to the stiffener, wherein each leg of the plurality of legs is configured to adjust a distance of the stiffener from the orthopedic fixation device;
a plurality of connectors for joining the plurality of legs to the orthopedic fixation device, wherein the plurality of connectors comprise a plurality of tapered collets, wherein each tapered collet of the plurality of tapered collets is adapted for receiving a leg of the plurality of legs and securing the leg of the plurality of legs to a pedicle screw of the plurality of pedicle screws; and packaging for holding the stiffener, the plurality of legs and the plurality of connectors, and for maintaining the stiffener, the plurality of legs, and the plurality of connectors in a sterile condition prior to use.

* * * * *

UNITED STATES PATENT AND TRADEMARK OFFICE
CERTIFICATE OF CORRECTION

PATENT NO. : 9,895,174 B2
APPLICATION NO. : 15/127086
DATED : February 20, 2018
INVENTOR(S) : Ozdil et al.

It is certified that error appears in the above-identified patent and that said Letters Patent is hereby corrected as shown below:

In the Specification

In Column 1, Line 8, delete "filed March 18, 2014," and insert -- filed on March 18, 2014, --, therefor.

In Column 2, Line 53, delete "is perspective" and insert -- is a perspective --, therefor.

In Column 11, Line 33, delete "screws 14." and insert -- screws 12. --, therefor.

In Column 16, Line 1, delete "feet, By" and insert -- feet. By --, therefor.

In Column 26, Line 11, delete "recitation no" and insert -- recitation, no --, therefor.

In Column 26, Line 33, delete "general such" and insert -- general, such --, therefor.

In Column 26, Line 40, delete "general such" and insert -- general, such --, therefor.

Signed and Sealed this
Twenty-fourth Day of April, 2018

Andrei Iancu
*Director of the United States Patent and Trademark Office*